(12) United States Patent
Chang et al.

(10) Patent No.: US 8,306,184 B2
(45) Date of Patent: Nov. 6, 2012

(54) X-RAY PIXEL BEAM ARRAY SYSTEMS AND METHODS FOR ELECTRONICALLY SHAPING RADIATION FIELDS AND MODULATION RADIATION FIELD INTENSITY PATTERNS FOR RADIOTHERAPY

(75) Inventors: Sha X. Chang, Chapel Hill, NC (US); Ying Wu, Chapel Hill, NC (US)

(73) Assignees: The University of North Carolina at Chapel Hill, Chapel Hill, NC (US); Duke University, Durham, NC (US)

( * ) Notice: Subject to any disclaimer, the term of this patent is extended or adjusted under 35 U.S.C. 154(b) by 528 days.

(21) Appl. No.: 11/921,294

(22) PCT Filed: May 31, 2006

(86) PCT No.: PCT/US2006/021009
§ 371 (c)(1),
(2), (4) Date: Aug. 3, 2009

(87) PCT Pub. No.: WO2006/130630
PCT Pub. Date: Dec. 7, 2006

(65) Prior Publication Data
US 2010/0260317 A1   Oct. 14, 2010

Related U.S. Application Data

(60) Provisional application No. 60/685,791, filed on May 31, 2005.

(51) Int. Cl.
*G01N 23/04* (2006.01)
*H05G 1/70* (2006.01)
*A61N 5/10* (2006.01)

(52) U.S. Cl. .............. 378/62; 378/92; 378/65

(58) Field of Classification Search .......... 378/62, 378/92, 65, 119, 138, 137
See application file for complete search history.

(56) References Cited

U.S. PATENT DOCUMENTS

| 4,286,192 A * | 8/1981 | Tanabe et al. ............ 315/5.41 |
| 4,327,293 A | 4/1982 | Taumann |

(Continued)

OTHER PUBLICATIONS

International Preliminary Report on Patentability for PCT Application No. PCT/US2006/021009 dated Dec. 21, 2007.

(Continued)

*Primary Examiner* — Irakli Kiknadze
(74) *Attorney, Agent, or Firm* — Jenkins, Wilson, Taylor & Hunt, P.A.

(57) ABSTRACT

X-ray pixel beam array systems and methods for electronically shaping radiation fields and modulating radiation field intensity patterns for radiotherapy are disclosed. One exemplary pre-clinical system may include addressable electron field emitters (102, 104) that are operable to emit a plurality of electron pixel beams (106, 108, 110). Each electron pixel beam may correspond to an x-ray target (124) and x-ray pixel beam collimation aperture (136, 138) to convert a portion of energy associated with the electron pixel beam to a corresponding x-ray pixel beam (140, 142). Further, the x-ray pixel beam array collimator (130) forms a one-to-one correspondence between individual electron pixel beam and its corresponding x-ray pixel beam. One exemplary clinical system may include a high-energy electron source (1203), an n-stage scanning system (1210), x-ray pixel beam targets (1212), and an x-ray pixel beam array collimator (1214). A controller (1206) may sequentially direct electron beam pulses to pre-determined x-ray pixel targets and produce an electronically controlled radiation field direction, pattern; and intensity pattern.

35 Claims, 15 Drawing Sheets

U.S. PATENT DOCUMENTS

| | | | |
|---|---|---|---|
| 5,228,068 | A | 7/1993 | Mazess |
| 5,511,105 | A | 4/1996 | Knott |
| 5,585,642 | A * | 12/1996 | Britton et al. ............... 250/492.3 |
| 5,754,622 | A * | 5/1998 | Hughes ........................... 378/65 |
| 6,175,615 | B1 | 1/2001 | Guru et al. |
| 6,265,837 | B1 * | 7/2001 | Akiyama et al. ............. 315/503 |
| 6,333,968 | B1 | 12/2001 | Whitlock et al. |
| 6,487,274 | B2 * | 11/2002 | Bertsche ....................... 378/143 |
| 6,553,096 | B1 | 4/2003 | Zhou et al. |
| 6,630,678 | B2 * | 10/2003 | Guzorek ................... 250/432 R |
| 6,787,122 | B2 | 9/2004 | Zhou |
| 6,850,595 | B2 | 2/2005 | Zhou et al. |
| 7,455,757 | B2 | 11/2008 | Oh et al. |

OTHER PUBLICATIONS

International Search Report for PCT/US2006/021009 dated Feb. 15, 2007.

Saito, Y., S. Uemura, and K. Harnaguchi, *Cathode Ray Tube Lighting Elements with Carbon Nanotube Field Emitters*, Jpn. J. Appl. Phys., 1998.37: p. L346-348.

Bower, C., et aL, *Synthesis and Structure of Pristine and Cesium Intercalated Single-Walled Carbon Nanotubes*. Applied Physics, 1998. A67: p. 47-52.

Zhu, W., et aL, *Very high current density from carbon nanotube field emitters*. AppL Phys. Lett., 1999. 75(6): p. 873-875.

Tang, X.P., et aL, *Electronic structures of single-walled carbon nanotubes determined by NMR*. Sdence, 2000. 288: p. 492.

Gao, B., et aL, *Fabrication and electron field emission properties of carbon nanotube films by electrophoretic deposition*. Adv. Mater., 2001. 13(23): p. 1770-1774.

Yue, G.Z., et al., *Generation of continuous and pulsed diagnostic imaging x-ray radiation using a carbon-nanotube-based field-emission cathode*. Appl. Phys. Let~., 2002. 81 (2): p. 355.

Zhou, O., et al., *Materials Science of Carbon Nanotubes: Fabricatiof), Integration, and Properties of Macroscopic Structures of Carbon Nanotubes*. Acc. Chern. Res, 2002. 35: p. 1045-1053.

Y. Cheng and O. Zhou, Field emission from carbon nanotubes. C. R. Physique, 2003. 4: p. 1021-1033.

Y. Cheng, et al., *dynamic X-ray radiography using a carbon nanotube field emission x-ray source*. Rev. Sci. Inst., 2004. 75(10): p. 3264.

J. Liu, et al., U.S. Appl. No. 60/531,978, "*Method of synthesizing small-diameter carbon nanotubes with enhanded electron field emmision properties*".

* cited by examiner

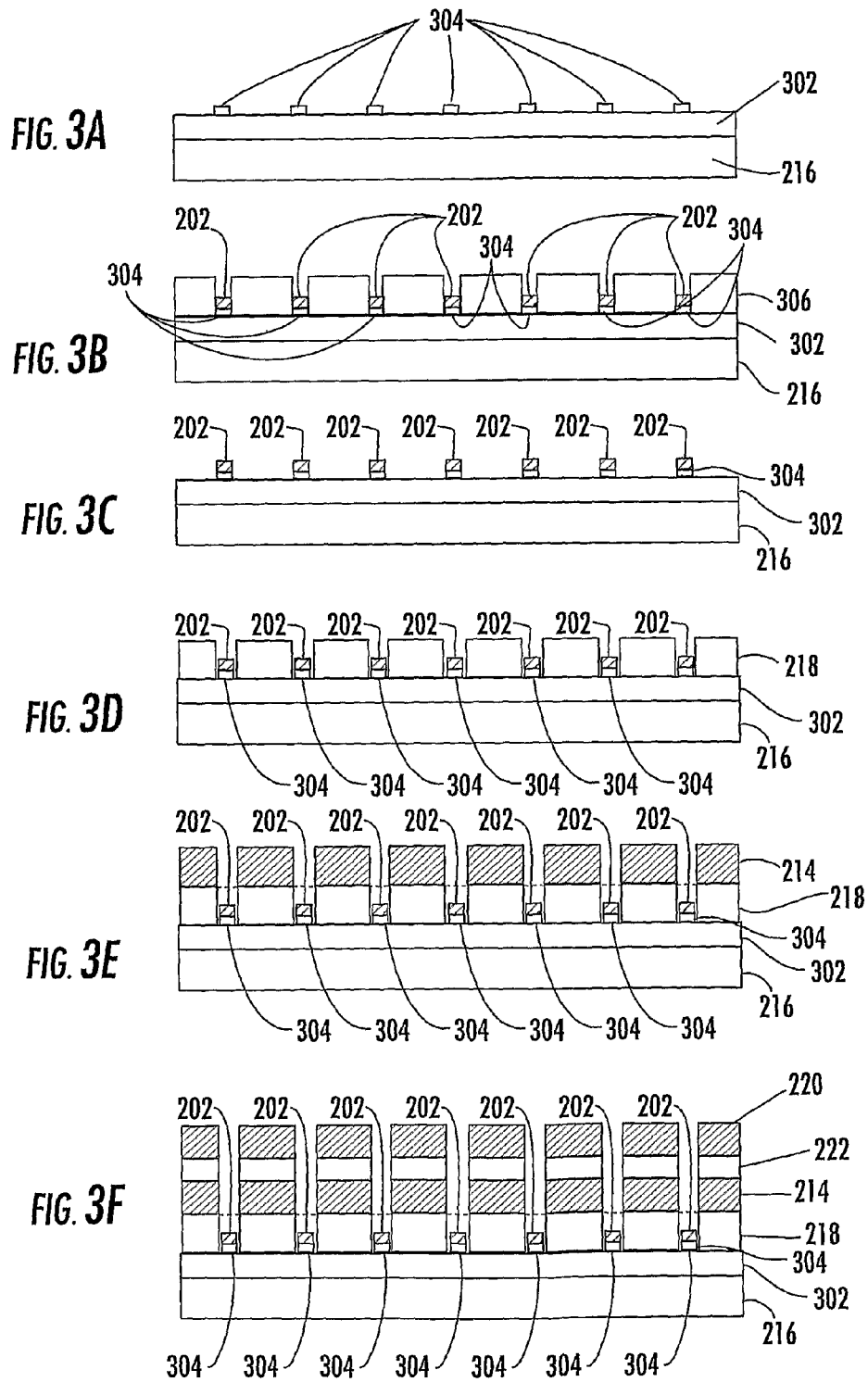

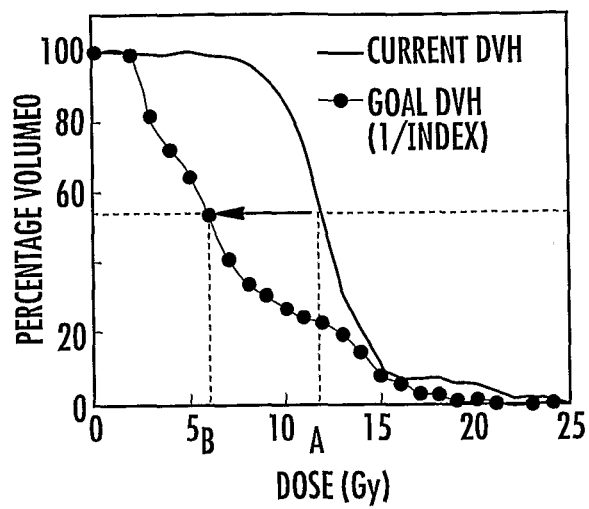
FIG. 11A
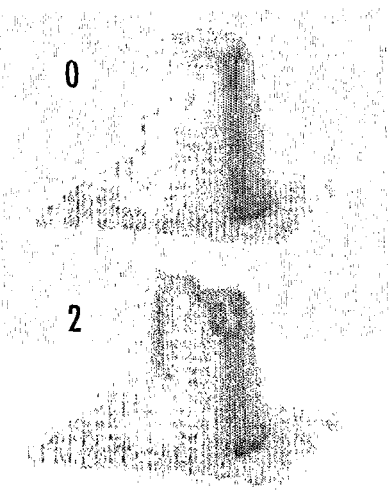
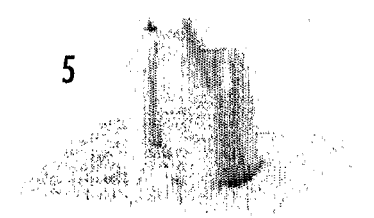
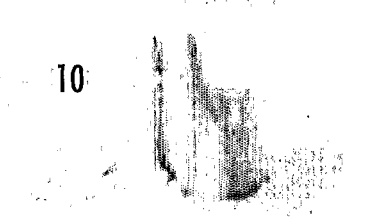
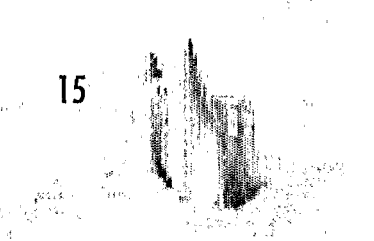
FIG. 11B

X-RAY PIXEL BEAM ARRAY SYSTEMS AND METHODS FOR ELECTRONICALLY SHAPING RADIATION FIELDS AND MODULATION RADIATION FIELD INTENSITY PATTERNS FOR RADIOTHERAPY

CROSS-REFERENCE TO RELATED APPLICATION

This non-provisional patent application claims the benefit of U.S. Provisional Application No. 60/685,791, filed May 31, 2005, the disclosure of which is incorporated by reference herein in its entirety.

TECHNICAL FIELD

The subject matter disclosed herein relates to using x-rays for radiotherapy treatment in clinical and pre-clinical use. More particularly, the subject matter disclosed herein relates to x-ray beam pixel array systems and methods for electronically shaping radiation fields and intensity modulation patterns for clinical and pre-clinical radiotherapy applications.

BACKGROUND ART

Many cancer patients receive radiotherapy (RT) during the course of cancer treatment. RT may be used alone or combined with other treatment modalities. Despite the significant advances in cancer diagnosis, treatment technologies, and research in recent years, the age-adjusted cancer death rate in the United States has not shown a corresponding improvement. Further, quality of life issues have been receiving a growing amount of attention from cancer patients and healthcare providers. Today, the consideration of quality of life is an important factor for many cancer patients and their healthcare providers in choosing cancer management techniques.

Pre-Clinical RT Devices

Improvements in cancer patient survival and quality of life require translational research that assesses tumor control and normal tissue toxicity from a particular treatment concurrently, especially in the case of combined drug and radiation treatment. In addition to the existing cancer fighting drugs, the advances in basic cancer biology, pharmacology, and nanomedicine are expected to produce new promising biomarkers/biosensors, nano-scale agents with cancer-specific imaging contrast, agents loaded with potent cancer killing drugs, radiosensitizers, and radioprotectors. These future cancer-fighting and radiological countermeasure drugs underscore the need to develop new research tools that can facilitate comprehensive and clinically relevant preclinical studies that will be required to evaluate the immediate and long-term effects of these agents on both tumor and normal tissues.

Small animal models have been widely used for basic cancer research. Human tumor xenografts in small animals are commonly used to study drug and radiosensitization efficacy. However, the standard xenograft model of implanting tumor cells at various sites of immunocompromised mice has inherent limitations in that, while easily accessible for irradiation and measurement, tumors created from established cell lines implanted into non-native sites can respond differently than spontaneous tumors arising in their native environment. Recently, orthotopic models have been developed in which cancer types common to humans, such as small cell lung or prostate carcinoma, may be genetically produced in mice. In this case, however, monitoring tumor size by palpation is difficult or impossible for non-superficial sites. Thus, sophisticated, high-resolution imaging tools are required to evaluate response to treatment in most orthotopic tumor models. Furthermore, delivery of radiotherapy for radiosensitization studies using orthotopic models is complicated by the radiation toxicity associated with many sites. Targeted radiotherapy delivery, with confirmation of adequate treatment of the tumor while sparing adjacent normal tissues has been a primary limitation to such studies. Tools are desirable that can provide animal models that may be used to study the interaction between drugs and radiation, as well as provide information for drug development and human clinical application. Appropriate animal models can also be used to study other cancer treatment topics that cannot be adequately addressed by clinical trials. For example, whether new technologies in radiotherapy, especially those with high cost, generate real benefit in terms of local tumor control and quality of life.

One cancer research tool is a small animal irradiator. Current small-animal irradiators, such as Cesium-137 irradiators, have spatial resolution of 1 cm at best and have practically no temporal control for a given radiation dose. Often mouse irradiation intended for the tumor is also unavoidably given to the entire body or a large portion of it. Consequentially severe radiation reactions are prone to develop in the mouse model that can greatly hinder the range of study possible. In human radiotherapy treatment, toxicity is minimized and tumor control is maximized by using state of the art image-based treatment optimization design and high precision delivery technologies. One example is dose optimized conformal radiotherapy, where the radiation dose "wraps around" the tumor and largely avoids critical structures and normal tissues. Because of the lack of imaging devices in most animal model research laboratories, many orthotopic models with internal tumors that are not easily palpable cannot be used for irradiation study. Conformal and fractionated irradiation, as used in human radiotherapy, is also not possible in current small animal irradiation technology. Such technical limitations prevent researchers from fully using the animal models under conditions analogous to those used for human treatment, thereby weakening the clinical relevancy of the research.

Realizing the existing gaps in small animal irradiation technology, one researcher began to develop a micro-RT device using the readily available brachytherapy isotope Ir-192 as the radiation source. The radiation field may be shaped to selected sizes by using a set of physical collimation cones that are suitable for small animal irradiation. Another researcher proposed a combined imaging and irradiation micro-CT-RT small animal research platform where conventional kV x-ray tubes are used for CT imaging and irradiation. There are considerable technical challenges in developing these proposed small animal irradiation and imaging devices to meet the spatial and temporal resolution demands of high quality small animal imaging and conformal irradiation. One challenge is related to the mechanical complexity in the design, fabrication, and control of the miniaturized radiation field collimation system. Assuming that the micro-RT system includes features similar to linear accelerators for human RT, that is, with the high accuracy and automatic collimator motion needed for intensity-modulated treatment, the miniature scale involved in micro-RT irradiation of small animals would be difficult to develop. Another challenge is the temporal resolution required for high quality imaging and image-guided conformal irradiation of live small animals capable of rapid organ motion. Conventional x-ray tubes deliver continuous radiation and thus can lead to motion-blurred images. In addition, the radiation dose from imaging alone may be high. Pulsed irradiation lasting only a fraction of the organ motion cycle is better suited for such imaging and results in less total dose to the animal.

Clinical RT Devices

Medical linear accelerators (LINACs) are the main clinical RT devices in the United States and many other countries. A conventional RT LINAC primarily consists of three major moving components: (1) a treatment table in a horizontal position to hold the patient under the radiation beam; (2) a gantry system that can be rotated in a vertical plane and from which a radiation beam is aimed at the patient on the treatment table; and (3) a physical beam collimator system (at the end of the gantry) that mechanically defines the shape and location of the radiation field. Each of the three moving components can rotate about its own rotation axis and all three axes meet at one point in space, which is referred as the LINAC isocenter. Often, a patient is setup for treatment so that the isocenter is inside the treatment target tumor. Using this conventional LINAC system a typical RT treatment consists of 3-6 radiation fields. Each field enters the patient from a different angle to form a conformal radiation distribution around the treatment target volume. The radiation collimation devices of a LINAC may include movable jaws, lead alloy custom blocks, and automated multi-leaf collimator (MLC) systems. A MLC system can be consist of more than 100 pairs of individual collimator leaves, each leaf is controlled by a motor that drives the leaf motion and an encoder that reads the position of the MLC leaf. For intensity-modulated radiotherapy (IMRT), a treatment that is designed to maximize both the tumor control and normal tissue sparing, the MLC leaves are programmed to move with predefined pattern and speed during or between radiation deliveries. Therefore, modern conventional clinical LINAC is very complicated mechanically and electronically, and the there are mechanical constraints on MLC motion (configuration and speed) so that some radiation field configurations and intensity patterns are not physically possible.

Recently, a new type of clinical LINAC called Tomotherapy has received wide acceptance. A Tomotherapy unit resembles more of a CT scanner than the conventional clinical LINAC. Within a donut structure, the RT x-ray accelerating waveguide physically rotates around the patient, similar to the x-ray tube rotating inside a CT scanner. The high energy RT x-rays are used radiation treatment and CT imaging. Tomotherapy uses the same mechanical means approach as conventional clinical LINAC for radiation field shaping and intensity modulation.

X-ray imaging and CT imaging are increasingly used in RT cancer treatment to accurately align patient with radiation fields in the fractionated treatment course. This new technology is referred as Image-Guided Radiotherapy (IGRT). IGRT has the potential to significantly increase the quality of highly conformal and intensity-modulated treatment by accurately aligning the patient under radiation beams in daily treatment. Currently, RT treatment imaging can be done using several methods including a separate CT scanner placed inside the treatment room, a kV x-ray imaging system attached to the treatment accelerator, and an imaging system using directly the treatment beam, as in the case of Tomotherapy. These IGRT methods all rely on a mechanically rotating x-ray source for imaging. Both the conventional clinical LINAC and Tomotherapy use mechanical motion of MLC leaves to define radiation field shape and its intensity distribution.

In all existing RT technologies, x-rays are controlled by mechanical means—the direction from which the x-ray radiation field arrived (gantry), the radiation field shape (MLC), and the radiation intensity distribution within the field (MLC). This dependence on mechanical means hinders the advancement of the RT technologies to meet the increasing demand to deliver RT treatments with higher spatial and temporal resolution for better treatment outcome. The increasingly complex mechanical components and thus their electronic control systems can also significantly raise the cost of cancer treatment (device purchase cost and the ongoing maintenance cost include technical staff) and at the same time drop reliability of the RT machine.

Accordingly, there exists a need for technology that forms the spatial and temporal feature of RT x-ray radiation field electronically without mechanical motion. In pre-clinical RT application, it is desirable to have technology operable to provide high-resolution conformal irradiation to small animal models for making animal model studies more clinically relevant. In the clinical application, it is desirable to have technology for leading to a new generation of clinical RT devices that can better meet the increasingly high demand on radiation manipulation and cancer treatment cost containment.

SUMMARY

According to one aspect, the subject matter described herein includes x-ray array systems and methods for electronically shaping radiation fields and modulating radiation field intensity patterns for radiotherapy. One pre-clinical x-ray pixel array system includes a plurality of addressable electron field emitters operable to emit a plurality of electron pixel beams. An anode may be positioned to accelerate electrons associated with the electron pixel beams and to convert a portion of energy associated with the electron pixel beams to x-ray pixel beams. An x-ray pixel array collimator may be positioned to collimate the x-rays generated from electron pixel beams into output a plurality of collimated x-ray pixel beams. The collimator is structured such that a one-to-one correspondence exists between an electron pixel beam and an x-ray pixel beam. A controller may be operable to individually control electron emission from each of the electron field emitters for selectively generating a set of x-ray pixel beams and an intensity pattern of the set of x-ray pixel beams.

A clinical x-ray pixel array system according to the subject matter described herein may include a pulsed MeV electron beam source generated by a linear accelerator operable to produce a pulsed electron beam. An n-stage scanning system may be operable to scan the electron beam along a path, wherein n is an integer of at least two. A plurality of x-ray targets may be positioned to convert the electron beam to an x-ray pixel beam. An x-ray pixel array collimator may be positioned downstream of the x-ray targets to collimate the x-ray beam for producing an x-ray pixel beam. A controller may be operable to control the pulsation of the electron beam source and the n-stage scanning system for sequentially generating a predetermined spatial and intensity x-ray pixel beam array pattern.

An x-ray pixel beam array system according to the subject matter described herein may be used for imaging a subject. The system may include a pulsed MeV electron beam source generated by a linear accelerator operable to produce a pulsed electron beam. Further, the system may include an n-stage scanning system operable to scan the electron beam along a path, wherein n is an integer of at least two. A plurality of x-ray targets may be positioned to receive the electron beam and convert at least a portion of energy associated with the electron beam to imaging x-ray beams from different angles. A controller may be operable to control the pulsation of the electron beam source and operable to control the scanning system for producing imaging x-rays from predetermined directions to image a subject. The system may include a rotating x-ray image plate for image acquisition of the subject.

BRIEF DESCRIPTION OF THE DRAWINGS

Preferred embodiments of the subject matter described herein will now be described with reference to the accompanying drawings, of which:

FIGS. 3A-3F are steps of a method for fabricating multiple electron field emitters, a gate electrode, and a focusing electrode according to an embodiment of the subject matter described herein;

FIG. 11A is a graph of a goal DVH curve and the current DVH that changes in the optimization according to the subject matter described herein;

FIG. 11B shows intensity maps of a radiation field after n iterations in the optimization according to the subject matter described herein;

DETAILED DESCRIPTION

Figure 1:
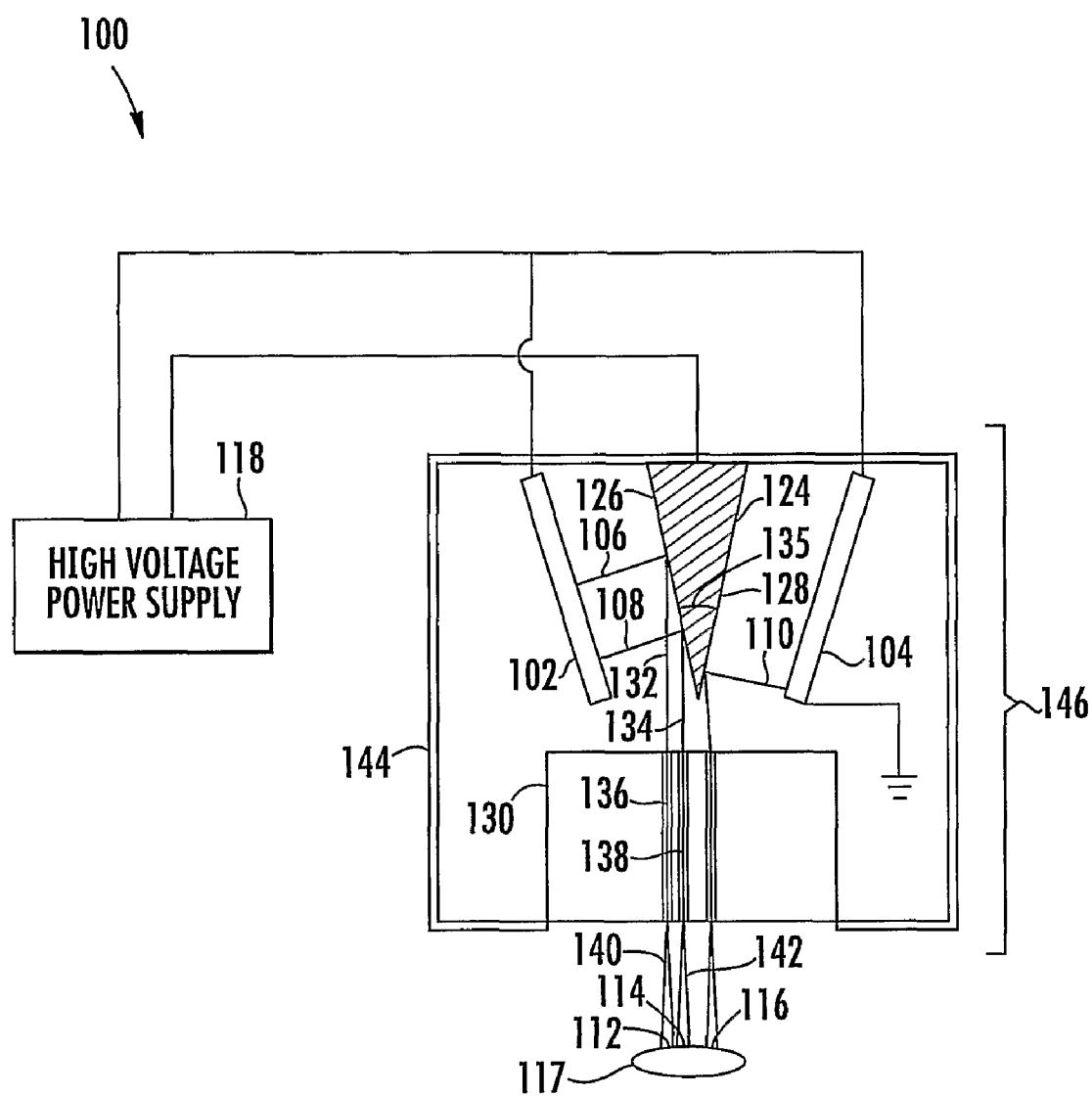
FIG. 1 is a schematic, cross-sectional side view of an x-ray pixel array system suitable for pre-clinical applications according to an embodiment of the subject matter described herein.

In accordance with the present disclosure, x-ray pixel array systems and related methods are provided. The systems and methods described herein may have particular application for use in electronically shaping radiation field and modulating radiation intensity pattern for subject irradiation. CT imaging and radiotherapy (RT) treatment are exemplary uses of the systems and methods described herein. In particular, the systems and methods described herein may be used for delivering radiation to animals in a pre-clinical setting and/or humans in a clinical setting.

For a pre-clinical application, an x-ray pixel array system according to the present disclosure may include a plurality of addressable electron field emitters operable to emit a plurality of electron pixel beams. Further, an x-ray pixel array system according to the present disclosure may include an anode positioned to accelerate electrons in the electron pixel beams and to convert a portion of energy associated with the electron pixel beams to x-ray beams. An x-ray pixel array collimator may be positioned to receive the x-ray beams and to output a plurality of collimated x-ray pixel beams. The collimator may be structured such that a one-to-one correspondence exists between an electron pixel beam and an x-ray pixel beam. Further, a controller may be operable to individually control electron emission from each of the electron field emitters for generating a specific shape and intensity pattern of radiation field that is made of many x-ray pixel beams. Further, aspects of an radiation field may be controlled, such as the absolute dose, the size, the shape, and the intensity distribution of the radiation field by the controller.

For a clinical application, an x-ray pixel array system according to the present disclosure may include an electron source operable to emit an electron beam. Further, the x-ray pixel array system may include a linear accelerator for electron acceleration. The system may also include an n-stage scanning system, n being an integer of at least two, operable to receive the electron beam and to convert at least a portion of energy associated with the electron beam to an x-ray beam. An x-ray pixel array collimator may be positioned to collimate x-rays produced by scanning electron beam to x-ray pixel beam. A controller may be operable to control the scanning system for sequentially directing the electron beam to the predetermined x-ray targets and produce the desired x-ray pixel beam irradiation pattern. The scanning system may be controlled to direct the x-ray beam along a particular path such that a collimated x-ray beam is produced along the path to irradiate a predetermined location for a predetermined duration and radiation dosage using a predetermined sequence. Further, aspects of an applied radiation field may be controlled, such as the absolute dose, the size, the shape, and the intensity distribution of the radiation field.

An x-ray pixel array system for imaging a subject according to the subject matter described herein may include an electron source operable to emit an electron beam. Further, the system may include a linear accelerator for electron acceleration. The system may also include an n-stage scanning system, n being an integer of at least two, operable to scan the electron beam along a path. Further, an x-ray target may be positioned to receive the collimated electron beam and to convert at least a portion of energy associated with the electron beam to an x-ray beam to image a subject. The system may include an x-ray imaging plate for detecting the x-ray beam to produce an image of the subject.

X-Ray Pixel Array System for Pre-Clinical Applications

As described above, according to one aspect, the subject matter described herein includes an x-ray pixel array system for pre-clinical applications. Such a system with electronic and individual control of x-ray pixel beam may be suitable for electronically shaping radiation field and modulating radiation intensity pattern for small animal irradiation in pre-clinical studies. For the desired energy level to be delivered to the target is on the order of kilo-electron volts (keV). However, the pre-clinical x-ray pixel systems and methods described herein are not limited to pre-clinical applications.

FIG. 1 illustrates a schematic, cross-sectional side view of an x-ray pixel array system suitable for pre-clinical applications and generally designated 100 according to an embodiment of the subject matter described herein. Referring to FIG. 1, system 100 may include two-dimensional (2-D) electron field emitter arrays 102 and 104. Arrays 102 and 104 may include a plurality of individually addressable and controllable electron field emitters for selectively generating collimated electron beams. For example, array 102 may generate electron pixel beams 106 and 108. Further, for example, array 104 may generate electron pixel beam 110. As described in further detail herein, the electron field emitters of arrays 102 and 104 may be attached to a surface of a cathode, conductive or contact line, or other suitable conductive material. The cathodes may be attached to a suitable non-conductive substrate such that the electron field emitters are electrically isolated.

Electron pixel beams 106, 108, and 110 of arrays 102 and 104 may be individually and electronically controlled (i.e., turned on and off). The beams of arrays 102 and 104 may be controlled for selectively irradiating predetermined locations 112, 114, and 116 on an object 117. A high voltage power supply 118 may control the application of high voltages between cathodes of arrays 102 and 104, respectively, and an anode 124. Further, a controller may control the operation of high voltage power supply 118. The voltage accelerates electrons emitted from the field emitters of arrays 102 and 104 to a higher energy. The voltage potential between an emitter and anode 124 can range from about 60 kV to about 100 kV for pre-clinical applications.

Anode 124 is an x-ray target that converts a portion of the energy of electron pixel beams to x-rays. For example, anode 124 can convert a portion of the energy of electron pixel beams 106 and 108, to x-rays 132 and 134, respectively. Anode 124 may include surfaces 126 and 128 positioned for intercepting electron beams emitted by arrays 102 and 104, respectively. For example, anode 124 may comprise a tungsten, gold, or molybdenum or alloy material that decelerates electrons emitted from array 102 and converts a portion of the energy associated with the electron pixel beam into x-rays. It is noted that the lines designated 132 and 134 indicate only the directions where the x-ray intensity is strong; the x-rays generated are not focused but broadly distributed in a wide solid angle range. Further, surfaces 126 and 128 may be positioned such that at least a portion of the x-ray pixel beams are directed in paths towards an x-ray pixel array collimator 130. For example, electron pixel beams 106 and 108 from array 102 can interact with anode 124 and generate intrinsic x-rays 132 or 134 and x-ray pixel beams 140 and 142 downstream of 130, respectively.

An angle 135 between surfaces 126 and 128 may be determined based on the material of anode 124, the electron energy, and the design of the x-ray pixel beam array collimator 130 to produce the best one-to-one correlation between electron pixel beam and its x-ray pixel beam. For example, high probability x-ray production directions 132 and 134 may be aligned with apertures 136 and 138, respectively, of collimator 130. In this example, apertures 136 and 138 may collimate x-rays generated by electron pixel beams 106 and 108 into x-ray pixel beams 140 and 142, respectively. The apertures of collimator 130 may be tapered or conical in shape for dosimetry considerations. Exemplary collimator materials include tungsten, steel, and other x-ray attenuating materials.

Arrays 102 and 104, anode 124, and collimator 130 may be enclosed within an interior of a vacuum chamber 144. The interior of vacuum chamber 144 may be sealed and evacuated to achieve a desired interior pressure. Further, the interior of vacuum chamber 144 may have a pressure differential with its exterior. Chamber 144 and the components within chamber 144 may comprise the electron field emitter cathodes 102 and 104 and anode 124. Head 146 may be included inside the vacuum chamber 144. Alternatively, head 146 can be included and controlled in a system that includes multiple heads to selectively irradiate the subject from different directions. Schematic diagrams of systems that incorporate head 146 will be described below.

Figure 2:
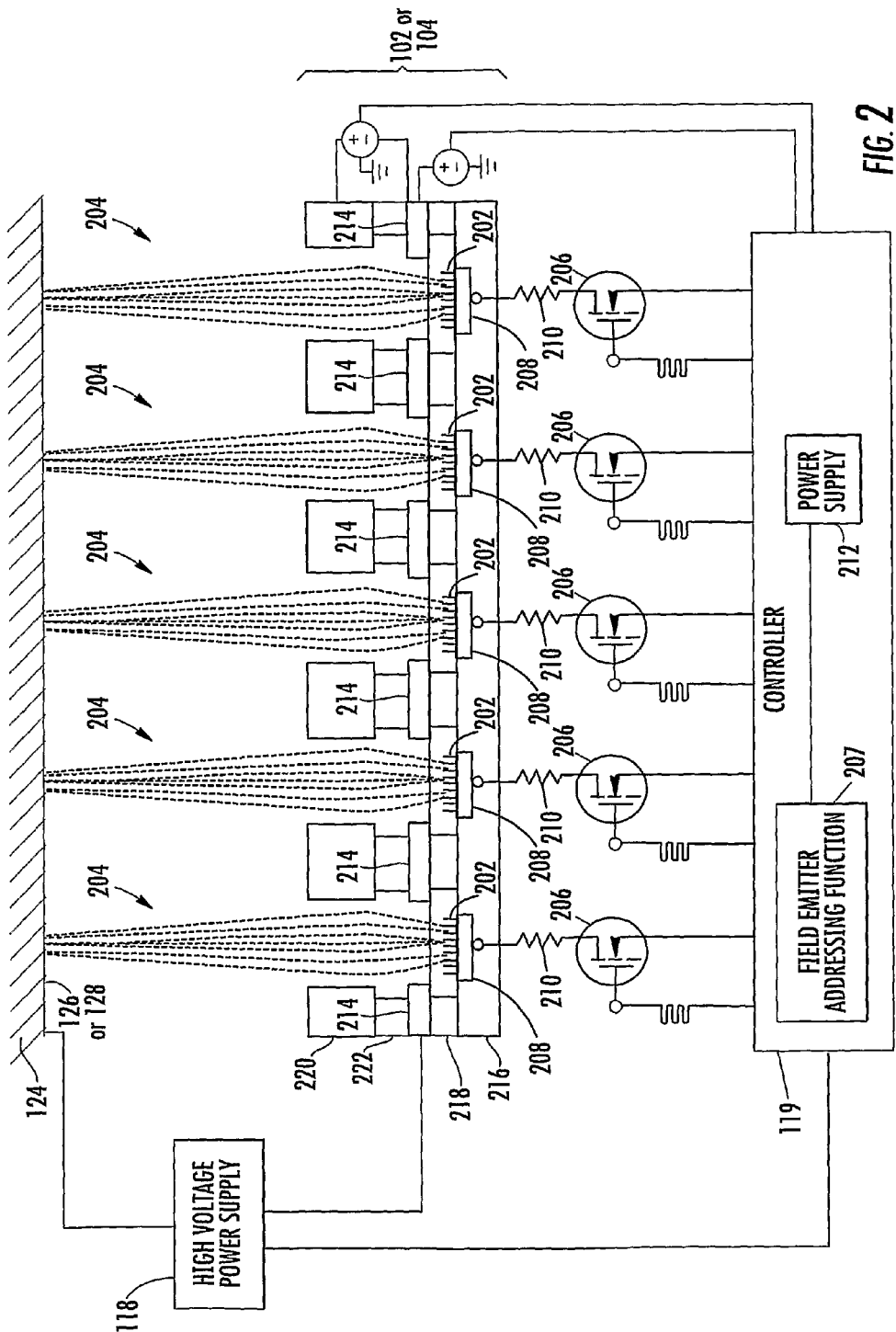
FIG. 2 is a schematic, cross-sectional side view of an electron field emitter array including a plurality of addressable electron field emitters according to an embodiment of the subject matter described herein.

FIG. 2 illustrates a schematic, cross-sectional side view of electron field emitter array 102 or 104 including a plurality of addressable electron field emitters according to an embodiment of the subject matter described herein. Referring to FIG. 2, array 102 or 104 may include a gate electrode 200 operable to extract electrons from field emitters 202 by generation of an electric field between gate electrode 200 and field emitters 202. After extraction from field emitters 202, the electrons may be directed by the generated electrical fields to travel along paths 204. Field emitters 202 may be spaced apart in an array or grid such that different locations of surface 126 or 128 of anode 124 intercept the emitted electrons. A controller 119 may be operable to individually control electron emission from each field emitter 202 for selectively emitting electron beams to intercept different locations of anode surface 126.

Controller 119 may individually operate a plurality of metal-oxide-semiconductor field-effect transistors (MOSFETs) 206 for individually addressing field emitters 202 to emit electrons. Controller 119 may include a field emitter addressing function 207 that individually switches on and off transistors 206. The drains of transistors 206 may be connected to a corresponding one of a plurality of cathodes 208. Each cathode 208 may be connected to a respective field emitter 202 via a resistor 210. Function 207 may control a power supply 212 to individually turn on and off power to the sources of transistors 206 for individually turning transistors 206 on and off. Transistors 206 may be turned on and off by the individual application of a high signal (e.g., 5V) and a low signal (e.g., 0 V), respectively, to the gates of transistors 206. When a high signal is applied to the gate of a transistor, a drain-to-source channel of the transistor is turned on to apply a voltage difference between a respective cathode 208 and a gate electrode 214. A voltage difference exceeding a threshold can generate an electric field between cathode 208 and gate electrode 214 such that electrons are extracted from respective electron field emitters 202. Conversely, when a low voltage (e.g., 0V) is applied to the gate of a transistor, a corresponding drain-to-source channel is turned off such that the voltage at a respective electron field emitter is electrically floating and the voltage difference between a respective cathode 208 and gate electrode 214 cannot generate an electric field of sufficient strength to extract electrons from the respective electron field emitter. Function 207 is operable to individually control the voltages applied to the gates of transistors 206. Thus, function 207 may individually address and control extraction of electrons from field emitters 202. To generate a scanning x-ray beam, a pulsed voltage with a predetermined pulse width may be scanned across the gate of a transistor. The transistor channel may be "opened" to generate an electron beam from a particular pixel. A scanning x-ray beam may be generated by sequentially activating individual pixels.

Cathodes 208 may be attached to a substrate 216 in an array spacing or a grid-like spacing. Substrate 216 may be made of silicon or any other suitable non-conductive substrate material for electrically isolating cathodes 208. A spacer 218 may be disposed between substrate 216 and gate electrode 214 for suitably spacing electron field emitters 202 and gate electrode 214. Spacer 218 may be made of an insulation material for electrically insulating substrate 216 and gate electrode 214.

A voltage difference may be applied between anode 124 and gate electrode 214 such that respective fields are generated for accelerating electrons emitted by electron field emitters 202 towards anode 126. The energy of the electrons may be adjusted by adjusting the electrical field strength applied between gate electrode 214 and cathode 208. The voltage between gate electrode 214 and cathode 208 may be adjusted to change the electrical field generated therebetween.

Array 102 or 104 can include a plurality of focusing electrodes 220 for at least partially focusing electrons emitted by respective electron field emitters 202. The electrons may be focused in a direction substantially towards respective locations on surface 126. A focusing electron voltage may be applied to focusing electrode 220 by power supply 212. Focusing electrode 220 may be made of any suitable conductive material, such as Al, Fe, Cu, and Mo. Focusing electrode 220 may be spaced from gate electrode 214 by a spacer 222 made of a suitable material for electrically isolating focusing electrode 220 and gate electrode 214.

Gate electrodes 214 and focusing electrodes 220 may each be formed of a single layer of conductive material. For example, gate electrodes 214 may be formed of a single layer of metal. Further, gate electrodes 214 and focusing electrodes 220 may each include apertures for providing a pathway for emitted electrons to travel from respective field emitters 202.

To minimize the fluctuation of x-ray flux, cathodes 208 may be operated in a constant current mode in which the gate voltage is automatically adjusted by controller 119 to maintain the emission current from each emitter within a desired level. Fluctuation may be minimized because the field emission from carbon nanotubes follows the Fowler-Nordheim equation which states that the emission current follows exponentially with the applied electrical field.

The dose delivered by each x-ray pixel beam can be controlled by providing control instructions for the emission current ($i_{a,i}$) and beam-on time ($t_i$) from the corresponding electron pixel, since the total dose from an x-ray pixel beam i is directly proportional to the product of current and time (IT), where IT=$I_{a,i}$×$t_i$. The relation between the radiation dose and IT may be calibrated per x-ray beam pixel under a predetermined calibration condition.

Calibration may be performed for each x-ray pixel beam. One of the x-ray pixel beams may be defined as a reference x-ray pixel beam (XPB$^{ref}$). The absolute dose output of the reference x-ray pixel beam may be calibrated per IT under a calibration condition. Exemplary calibration conditions may include a micro-RT isocenter, water equivalent phantom, and dose measurement depth of 15 mm. The dosimeter may be a gel detector or GAFCHROMIC™ film. The relative dose output of other x-ray pixel beams to the reference x-ray pixel beam may be measured under the calibration condition, except that the location of the dosimeter, as the ratio of $D^{XPB}_j$/ $D^{ref}$, wherein $D^{XPB}_j$ is the dose from the XPB$_j$ and $D^{ref}$ is the dose from the reference x-ray pixel beam. Once the calibration is complete, a controller may set the control parameter IT for each electron pixel to deliver a predetermined radiation. The irradiation time and current $i_a$ may be set to deliver a predetermined dose.

Gate electrodes, focusing electrodes, spacers, and other components of the arrays described herein may be fabricated by either bulk or surface micromachining techniques. Bulk micromachining generally involves sculpting one or more sides of a substrate to form desired three dimensional structures in the same substrate material. The substrate may be made of a material that is readily available in bulk form, such as silicon or glass. Wet and/or dry etching techniques may be employed in association with etch masks and etch stops to form microstructures and apertures within the material. Etching may be performed through the backside of the substrate. The etching technique may be either isotropic or anisotropic in nature. Etch masks and etch stops may be used to prevent predetermined regions of the substrate from being etched.

Conventional lithographic techniques may be employed in accordance with micromachining of the gate electrodes, focusing electrodes, collimators, anodes having electron permeable portions, spacers and other components of the multi-pixel electron microbeam irradiator systems described herein. Accordingly, basic lithographic process steps such as photoresist application, optical exposure, and the use of developers are not described in detail herein.

Similarly, generally known-etching processes may be employed to selectively remove material or regions of material. An imaged photoresist layer is ordinarily used as a masking template. A pattern may be etched directly into the bulk of a substrate, or into a thin film or layer that is then used as a mask for subsequent etching steps.

The type of etching process employed in a particular fabrication step (e.g., wet, dry, isotropic, anisotropic, anisotropic-orientation dependent), the etch rate, and the type of etchant used will depend on the composition of material to be removed, the composition of any masking or etch-stop layer to be used, and the profile of the etched region to be formed. As examples, poly-etch (HF:HNO$_3$:CH$_3$COOH) can generally be used for isotropic wet etching. Hydroxides of alkali metals (e.g., KOH), simple ammonium hydroxide (NH$_4$OH), quaternary (tetramethl) ammonium hydroxide ((CH$_3$)$_4$NOH, also known commercially as TMAH), and ethylenediamine mixed with pyrochatechol in water (EDP) may be used for anisotropic wet etching to fabricate V-shaped or tapered grooves, trenches or cavities. Silicon nitride is typically used as the masking material against etching by KOH, and thus may be used in conjunction with the selective etching of silicon. Silicon dioxide is slowly etched by KOH, and thus may be used as a masking layer if the etch time is short. While KOH will etch undoped silicon, heavily doped (p++) silicon may be used as an etch-stop against KOH as well as the alkaline etchants and EDP. A metal that may be used to form contacts and interconnects is gold, which is resistant to EDP. The adhesion layer applied in connection with forming a gold component (e.g., chromium) is also resistant to EDP.

It will be appreciated that electrochemical etching in hydroxide solution may be performed instead of timed wet etching. For example, if a p-type silicon wafer is used as a substrate, an etch-stop may be created by epitaxially growing an n-type silicon end layer to form a p-n junction diode. A voltage is applied between the n-type layer and an electrode disposed in the solution to reverse-bias the p-n junction. As a result, the bulk p-type silicon is etched through a mask down to the p-n junction, stopping at the n-type layer. Furthermore, photovoltaic and galvanic etch-stop techniques are also suitable.

Dry etching techniques such as plasma-phase etching and reactive ion etching (RIE) can also be used to remove silicon and its oxides and nitrides, as well as various metals. Deep reactive ion etching (DRIE) may be used to anisotropically etch deep, vertical trenches in bulk layers. Silicon dioxide may be used as an etch-stop against DRIE, and thus structures containing a buried silicon dioxide layer, such as silicon-on-insulator (SOI) wafers, may be used as starting substrates for the fabrication of microstructures.

An alternative patterning process to etching is the lift-off process. In this case, the conventional photolithography techniques are used for the negative image of the desired pattern. This process may be used to pattern metals, which are deposited as a continuous film or films when adhesion layers and diffusion barriers are needed. The metal may be deposited on the regions where it is to be patterned and on top of the photoresist mask (negative image). The photoresist and metal on top may be removed to leave behind the desired pattern of metal, such as the patterning of contact lines.

Suitable electron field emitters, such as carbon nanotubes, may be formed on conductive or semiconductive surfaces, such as contact lines and cathodes, described herein by electrophoretic deposition techniques and any other suitable techniques known to those of skill in the art, such as screen printing, chemical vapor deposition, and spraying. Generally, for example, carbon nanotubes may be electrophoretically deposited on a surface by a combination of some one or all of the following steps: (1) forming a solution or suspension containing the carbon nanotubes; (2) selectively adding "chargers" to the solution; (3) immersing electrodes in the solution, with the surface upon which the carbon nanotubes are to be deposited acting as one of the electrodes; (4) applying a direct and/or alternating current for creating an electrical field between the electrodes for a predetermined period of time to thereby cause the carbon nanotubes in the solution to migrate toward and attach themselves to the conductive or semiconductive surface; and (5) optional subsequent processing of the coated surface.

The electron emitters may be any suitable conductive structure and may have a sharp tip or protrusion for electron emission under an electrical field. Exemplary electron field emitters may include "Spindt" tips and other suitable nanostructures. "Spindt" tips and related processes are described in the publication "Vacuum Microelectronics," I. Brodie and C. A. Spindt, *Advances in Electronics and Electron Physics*, 83: 1-106 (1992), the disclosure of which is incorporated by reference herein. Exemplary materials of electron field emitter tips can include molybdenum (Mo), silicon (Si), diamond (e.g., defective CVD diamond, amorphic diamond, cesium-coated diamond, a nano-diamond), and graphite powders.

Nanostructures suitable for electron emission may include nanotube and nanowires/nanorods composed of either single or multiple elements, such as carbon nanotubes. A single carbon nanotube may have a diameter in the range of about 0.5-500 nm and a length on the order of about 0.1-100 microns.

Carbon nanotubes readily emit fluxes of electrons with small angular divergence. A carbon nanotube may include a single graphene shell, which is termed a single-wall carbon nanotube (SWNT), or multiple concentric grapheme shells, which is termed a multi-wall carbon nanotube (MWNT). A signature feature of carbon nanotubes is a large aspect ratio (ratio of diameter to length) that is typically on the order of $10^3$. Carbon nanotubes, nanowires and nanorods may be fabricated by techniques such as laser ablation, arc discharge, and chemical vapor deposition (CVD) methods. Further, carbon nanotubes may be made via solution or electrochemical synthesis. An exemplary process for fabricating carbon nanotubes is described in the publication "Materials Science of Carbon Nanotubes: Fabrication, Integration, and Properties of Macroscopic Structures of Carbon Nanotubes," Zhou et al., Acc. Chem, Res., 35: 1045-1053 (2002), the disclosure of which is incorporated herein by reference. A single carbon nanotube or a nanotube bundle may produce a current of about 0.1-10 µA.

Table 1 below summarizes the threshold field required to obtain a current density of 10 mA/cm² for several electron field emitter/cathode materials.

TABLE 1

Emission Threshold Field of Different Field Emitter/Cathode Material

| Electron Field Emitter/Cathode Material | Threshold Field (V/µm) for 10 mA/cm² |
|---|---|
| Mo Tips | 50-100 |
| Si Tips | 50-100 |
| p-type Diamond | 160 |
| Defective CVD Diamond | 30-120 |
| Amorphic Diamond | 20-40 |
| Cesium-coated Diamond | 20-30 |
| Graphite Powders | 10-20 |
| Nano-Diamond | 3-5 (unstable > 30 mA/cm²) |
| Assorted Carbon Nanotubes | 1-2 (stable > 4000 mA/cm²) |

Electron field emission is a quantum process where under an external electrical field electrons escape from a metal surface by quantum tunneling. Electron field emission may occur nearly instantly by external field control. The physics of field emission is summarized by the Fowler-Nordheim equation ($I = aV^2 \exp(-b\phi^{3/2}\beta V)$), stating that current (I) increases exponentially with increasing voltage (V). For a metal with a flat surface, the threshold field strength for field emission is typically around $10^4$ V/mm, which is impractically high to reach. For carbon nanotubes, due to their atomic sharp tips and large aspect ratios, they have much larger field enhancement factor β and thus a much lower emission threshold field that is practical to reach (~$10^2$ V/mm). Field-emitted electrons also have a very small energy spread of about 0.5 eV and a spatial divergence angle in a direction parallel to the electrical field of less than 5°.

An array of electron field emitters, a gate electrode, and a focusing electrode may be fabricated on a substrate by combination of electrophoresis and photolithography processes. Referring to FIGS. 3A-3F, a method for fabricating multiple electron field emitters, a gate electrode, and a focusing electrode according to one embodiment of the subject matter described herein is illustrated. In one example, the result is a 7×7 2-D electron field emitter pixel array having 1 mm pixels capable of emitting at least 2 mA peak current. Referring to FIG. 3A, substrate 216 may be provided, which may be a 4" silicon wafer, glass, or other suitable substrate. A thermal oxide layer 302 may be disposed on a top surface of substrate 216. Further, electrically-isolated conductive contact lines 304 may be disposed on a top surface of layer 302.

Referring to FIG. 3B, electron field emitters 202 may be deposited on a top surface of lines 304 by a photolithography/electrophoresis process. In one embodiment, a release/photoresist layer 306 may be deposited on portions of layer 302 that are not to be covered by electron field emitters 202. Further, in one embodiment, electron field emitters 202 may be carbon nanotubes. Next, referring to FIG. 3C, layer 306 may be removed without disturbing electron field emitters 202. An exemplary lithography and electrophoresis process for patterning carbon nanotubes is described in the publication "Liquid-Phase Fabrication of Patterned Carbon Nanotube Field Emission Cathodes," Oh et al., *Appl. Phys. Lett.*, 87(19): 3738 (2004), the disclosure of which is incorporated herein by reference in its entirety.

Referring to FIG. 3D, spacer 218 comprising a plurality of apertures corresponding to electron field emitters 202 may be disposed on the top surface of layer 302 between electron field emitters 202. Insulation layer 308 may be aligned using a mask aligner. In one embodiment, insulation layer 308 may be made of glass or any other suitable insulation material. Insulation layer 308 may be about 15 μm in thickness and patterned with an opening for exposing contact lines 304.

Referring to FIG. 3E, a gate electrode 214 comprising a plurality of apertures corresponding to electron field emitters 202 may be disposed on insulation layer 308. Next, referring to FIG. 3F, another insulation layer 310 and a focusing electrode 220 may be disposed on gate electrode 214. Insulation layer 310 and focusing electrode 220 can include a plurality of apertures corresponding to electron field emitters 202. An anode including a plurality of electron transparent windows may be fabricated. Each of the windows can correspond to one of electron field emitters 202. Alignment may be accomplished using alignment marks under a mask aligner and bonded together using a suitable wafer bonding technique.

According to one embodiment, electron field emitters 202 may be about 50-100 μm in diameter. Further, electron field emitters 202 may be electrically insulated from one another so that they may be individually addressed or controlled. Spacing between gate electrode 214 and electron field emitters 202 may be about 100 μm or any suitable distance such that a desired current may be reached with 1-2 kV driving voltage on gate electrode 214. Focusing electrode 220 can focus the field-emitted electrons on an anode surface.

In an alternate embodiment, insulation layer or spacer 218 and gate electrode 214 may be deposited on the top surface of layer 302 prior to the deposition of electron field emitters 202. Next, spacer 218 and gate electrode 214 may be covered by layers of resist and release materials. For example, contact lines 304, spacer 218, and gate electrode 214 may be spin-coated with a uniform layer of OMNICOAT™ release (available from MicroChem, Inc. of Newton, Me.). Next, contact lines 304, spacer 218, and gate electrode 214 may be spin-coated with a uniform layer of epoxy-based SU-8 negative photoresist product (available from MicroChem, Inc.) of about 10-20 mm in thickness. Depending on the desired SU-8 thickness, spin speed and viscosity of SU-8 may be controlled. The photoresist may be insoluble in alcohol. Next, the photoresist may be patterned by contact-mode UV photolithography and developed such that the area contact lines 304 to be deposited with electron field emitters 202 is removed while the other surfaces are covered with cross-linked SU-8. Subsequently, the exposed OMNICOAT™ release may be chemically removed to reveal contact lines 304. Next, electron field emitters 202 (in this example, carbon nanotubes) may be electrophoretically deposited onto contact lines 304 by applying a DC voltage between contact lines 304 and a counter-electrode submerged in alcohol containing carbon nanotubes. Further, $MgCl_2$ "chargers" may be added to the solution and a voltage applied between contact lines 304 and counter-electrode to cause the carbon nanotubes to deposit on contact lines 304. After deposition of the carbon nanotubes, the photoresist may be stripped using a release such as an OMNICOAT™ release.

Figure 4A:
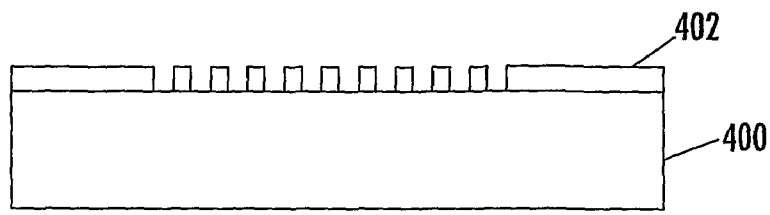
FIGS. 4A-4E are steps of a method for fabricating a gate electrode according to an embodiment of the subject matter described herein.
Figure 4B:
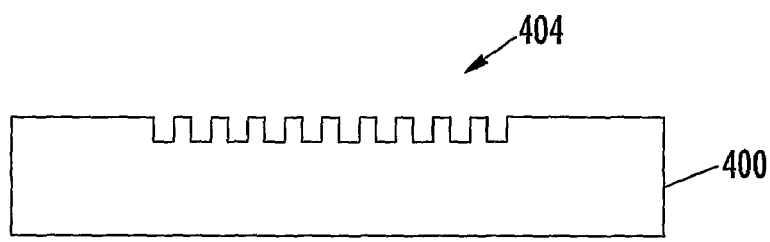
Figure 4C:
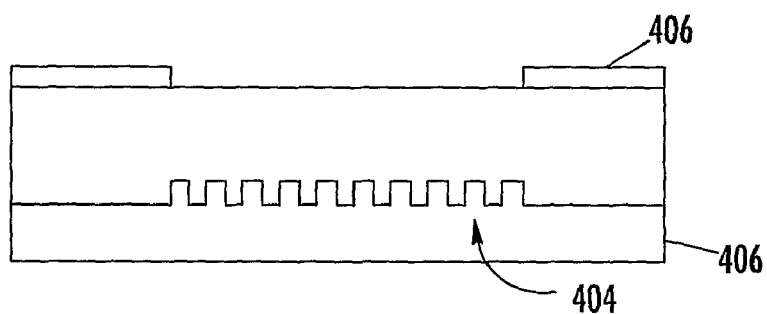
Figure 4D:
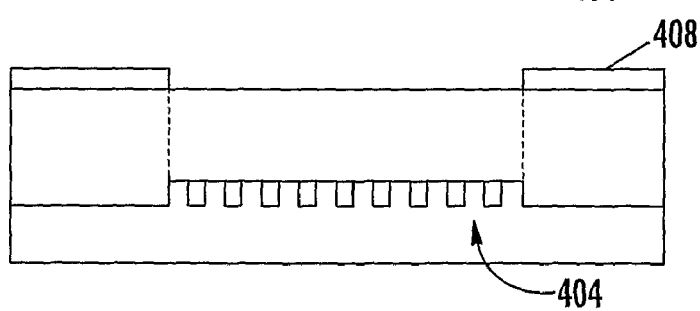
Figure 4E:
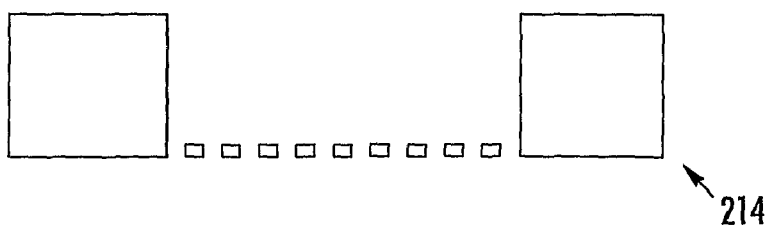

According to one embodiment, a gate electrode may be fabricated by combination of photolithography and deep reactive ion etch (DRIE) processes. Referring to FIGS. 4A-4E, a method for fabricating a gate electrode according to an embodiment of the subject matter described herein is illustrated. Referring to FIG. 4A, a substrate 400 may be provided, which may be a silicon wafer or other suitable substrate. Next, substrate 400 can patterned with an etch mask 402 for forming a metal mesh structure. Referring to FIG. 4B, a mesh structure 404 may be formed by performing a deep reactive ion etch. The etch may be about 50 μm deep. Referring to FIG. 4C, mesh structure 404 may be covered with a photoresist 406 and an opposing side of substrate 400 covered with an etch mask 408. Next, referring to FIG. 4D, a deep reactive ion etch may be performed from the opposing side until an aperture is formed to mesh structure 404. Referring to 4E, photoresist 406 and etch mask 408 may be removed for completing the fabrication of gate electrode 214.

Figure 5A:
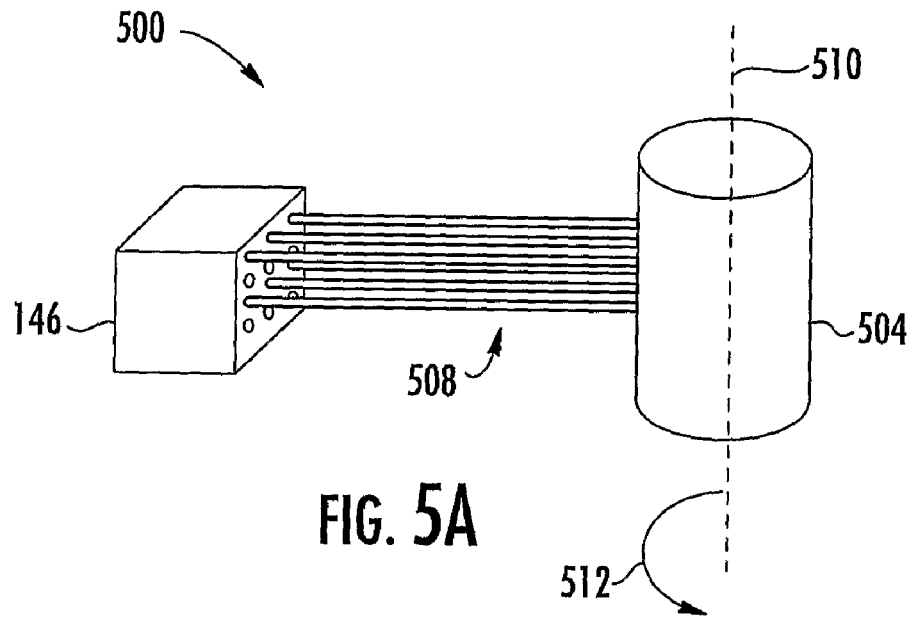
FIG. 5A is a schematic view of an x-ray pixel array system for irradiating predetermined locations of a subject according to an embodiment of the subject matter described herein.
Figure 5B:
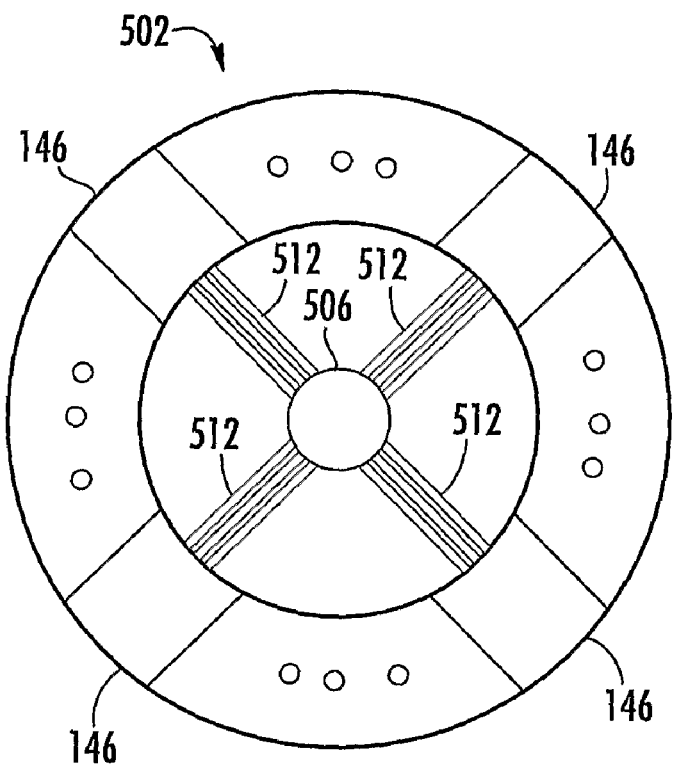
FIG. 5B is a schematic view of an x-ray pixel array system for irradiating predetermined locations of a subject according to an embodiment of the subject matter described herein.

FIGS. 5A and 5B illustrate schematic views of x-ray pixel array systems 500 and 502, respectively, for subject irradiation using electronically shaped radiation field and pixel beam intensity pattern. One or more head system 146 can be used according to an embodiment of the subject matter described herein. Referring to FIG. 5A, x-ray pixel array system 500 may include a head 146 producing a 2-D x-ray pixel array with a plurality of individually controllable x-ray pixel beams generally designated 508. X-ray pixel beams 508 may be directed to a subject within a treatment chamber 504. Chamber 504 may be controllably rotated about an axis 510 for irradiating the subject from different predetermined directions. A controller (not shown) may coordinate the rotation of chamber 504 with the activation of x-ray pixel beams for delivery of the predetermined treatment using the x-ray pixel beams to the subject within chamber 504.

Referring to FIG. 5B, x-ray pixel array system 502 may include a plurality of heads 146 that form a 360° circular x-ray pixel array having a plurality of individually controllable x-ray pixel beams for producing an x-ray beam array 512. X-ray pixel beam array 512 may be directed to a subject 506. Subject 506 may be positioned in about the center of the x-ray pixel beam array for receiving x-ray beams from several directions. The x-ray pixel beam intensity may be individually controllable by controller 119 for electronically shaping a radiation field and modulating intensity patterns for subject 506 from each predetermined radiation direction. For preclinical applications of conformal irradiation in small animals, such as mice, the field size of systems 500 and 502 may be about 10 mm×20 mm with an x-ray pixel beam size of about 2 mm in diameter.

Controlling Crosstalk between Electron Pixels and X-Ray Pixels

Crosstalk between an electron pixel beam and an x-ray pixel beam may be due to the angular distribution of Bremsstrahlung radiation created by the kV energy electrons and the finite linear attenuation coefficient of the collimator material. Some x-rays generated by an electron pixel beam may exit through adjacent apertures after traversing a part of the collimator wall between the adjacent apertures. The crosstalk can hinder the one-to-one correspondence between an electron pixel beam and an x-ray pixel beam producing undesirable background radiation that cannot be modulated. The following simulation is performed for a pre-clinical device. Similar simulations can be performed for a clinical device.

Figure 6A:
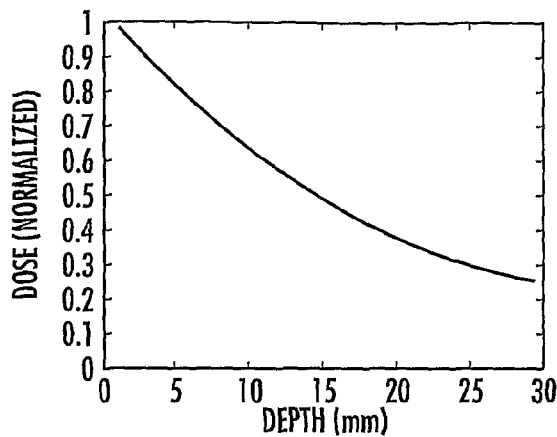
FIGS. 6A-6D are graphs showing Monte Carlo simulation results of dosimetric characteristics of an x-ray pixel array system in accordance with the subject matter described herein.

Monte Carlo simulations have demonstrated several dosimetric features of the systems and methods described herein. FIGS. 6A-6D are graphs showing Monte Carlo simulation results of dosimetric characteristics of an x-ray pixel array system in accordance with the subject matter described herein. The system includes individually controllable x-ray pixel beams that each have an energy of about 100 kV with standard filtration and a diameter of 2 mm at the system isocenter. The x-ray source-to-isocenter distance is 7 cm. FIG. 6A shows the percentage depth dose curve of an x-ray pixel beam in water. The radiation dose reduces to 50% of its maximum level as it reaches a depth of 15 mm.

Figure 6B:
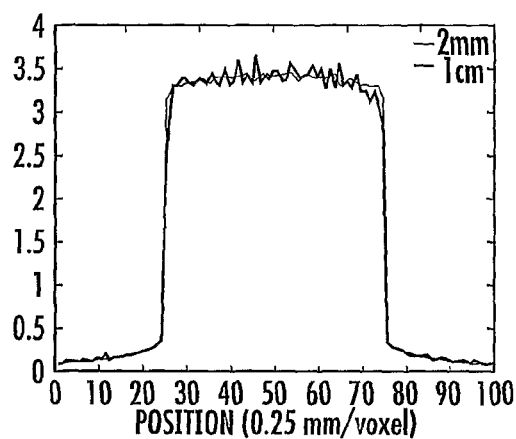

FIG. 6B shows the dose profile of a 10 mm×10 mm radiation field that is formed by an array of 25 2-mm x-ray pixel beams at a depth of 15 mm. The sharp beam penumbra of the individually controllable x-ray pixels can form arbitrary shaped treatment portal and generate intensity modulation patterns as shown in FIG. 6C with the given spatial resolution.

Figure 6C:
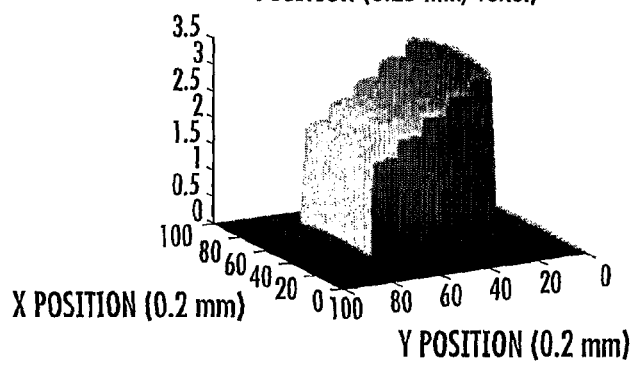
Figure 6D:
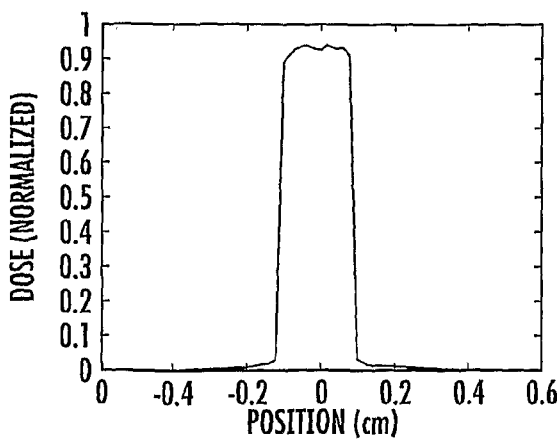

FIG. 6C shows the dose distribution of a wedge-shaped field formed by the x-ray pixel beam array. The treatment field is formed by an array of 5×5 x-ray pixel beams, each row of 5x-ray pixel beams uses a different beam-on time. FIG. 6D shows the dose profile of the 2 mm x-ray pixel beam at depth 15 mm.

Figure 7:
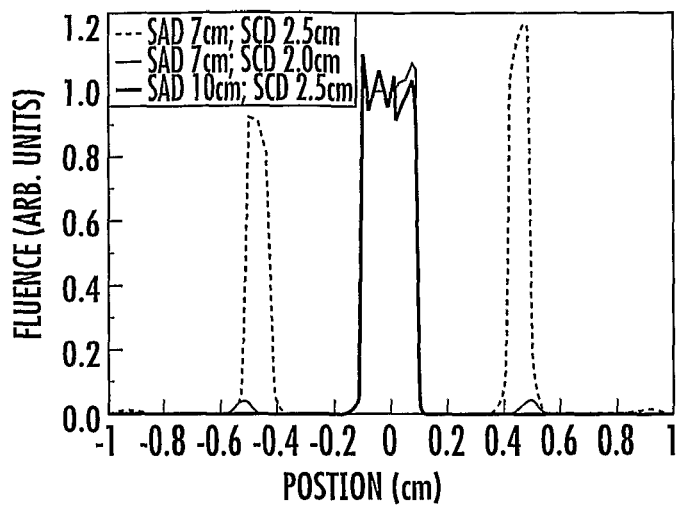
FIG. 7 is a graph showing a Monte Carlo simulation result for demonstrating the dependence of crosstalk on two design geometric parameters.

FIG. 7 illustrates a Monte Carlo simulation result that demonstrates the dependence of crosstalk on two design geometric parameters SAD and SCD, which denote the distance from where the x-ray pixel beam is created and the isocenter and the distance from where the x-ray is created and the bottom of the x-ray pixel array collimator, respectively. The simulation was performed on a system configured similar to system 100 shown in FIG. 1. In the simulation, angle 135 of system 100 was set to 15°. The diameters of the apertures of collimator 130 were set to 1 mm for projecting a beam size of 2 mm on the radiation subject at isocenter. The graph shows the fluence distribution for this baseline configuration at the isocenter plane. Further, the graph shows that reducing the source-collimator distance (SCD) from 2.5 cm (indicated by the dotted line) to 2.0 cm (indicated by the thin line) can significantly suppress crosstalk. Further, by increasing the x-ray source-to-isocenter distance (SAD) and the thickness of the collimator (indicated by the thick dashed line), crosstalk can be reduced to negligible levels.

Crosstalk may be reduced by using collimators made of high density materials. High density collimator materials can reduce the x-ray transmission between adjacent collimator apertures.

Spatial Resolution of Dose Deposition at Treatment Location

The x-ray pixel array systems described herein may be used for achieving high spatial resolution dose deposition. Spatial resolution is primarily determined by x-ray pixel beam size at isocenter and the electron transport property of the x-ray beams in the treatment volume. In one example, 100 kV x-ray pixel beams with filtration may be used for selectively removing the low energy portion of the x-ray beams.

Uniform Dose Distribution in the Treatment Volume

While the x-ray pixel beam array technology offers electronic definition of a radiation field, it lacks the intrinsic ability to achieve dose uniformity within a large field. Because of the finite x-ray source to isocenter distance, there is a divergence in each x-ray pixel beam. Thus, a single x-ray pixel beam array with many x-ray pixel beams may not be capable of generating uniform dose profiles at all distances from the x-ray source. FIG. 6B shows that, in the pre-clinical application, the cross-plane dose profiles from a 1 cm×1 cm radiation field formed by a 2 mm x-ray pixel beams are uniform. However, the beam profile is uniform only at isocenter plane and there can be significant peaks or valleys above or below isocenter. There is no solution to completely remove the dose inhomogeneity as long as there is divergence. Dose inhomogeneity may be reduced to acceptable levels by using of an opposing beam pair in animal irradiation, such that the dose peaks and valleys of one field are partially counteracted by the dose valleys and peaks of its opposing field, creating a more uniform cumulative dose distribution. Because of the large attenuation rate of the 100 kV x-ray in tissue, the dose peak/valley of one field cannot be neutralized completely by the valley/peak of the opposing field. Further, dose inhomogeneity may be reduced by using multiple treatment fields to weaken the effect of dose inhomogeneity from each individual field. Dose inhomogeneity may also be reduced by using intensity modulation.

Treatment Dose Rate on the Order of Gy/min or Higher

The maximum micro-RT (pre-clinical device) output rate may be determined by several factors including the maximum electron field emitter emission current density, the electron field emitter electron pixel size, the cooling efficiency of the anode, the size of x-ray pixel beam, and various other features of the x-ray pixel beam array design. FIG. 6D shows that a point dose is mostly from the primary x-ray pixel beam that passes through the collimator and that scatter dose from adjacent x-ray pixel beams is insignificant. In the Monte Carlo study described herein, an order of magnitude estimation has been made of the electron emission current required for the micro-RT to produce 1 Gy/min dose rate. A back-projection approach has been used for the estimation, which starts from dose deposition in tissue and back trace through the accelerator to the electron current that produces a required Bremsstrahlung radiation. The following assumptions were made in the estimation: (1) use of a 1 $mm^2$ carbon nanotube electron pixel; (2) 1% of the electron energy goes to Bremsstrahlung radiation; (3) 0.1% of the Bremsstrahlung radiation goes to the x-ray pixel beam; and (4) the linear attenuation coefficient of the 100 kV x-ray beam in tissue is 0.014/mm. It was concluded that the required micro-RT electron pixel current is between 1 μm and 1 mA for a dose rate in the order of 1 Gy/min, the human radiotherapy dose rate. A rectangular-shaped pixel may be 1 mm×4 mm in area with a long dimension in the direction of an anode wedge slope. If the x-ray is pulsed with a duty cycle of not less than 25%, experimental data indicates that the micro-RT is capable of reaching a dose rate of 1 Gy/min or higher.

Anode Heat Capacity

An anode temperature may increase due to electron bombardment. Anode heating can be significant in the pre-clinical application when the x-ray production yield is low. An anode may be cooled by utilizing one or more of several techniques. For example, the anode may be cooled by increasing its mass. In another example, the anode may be cooled by providing circulating water pipes inside the anode. Further, in another example, the anode may be cooled by providing a rotating anode.

Figure 8A:
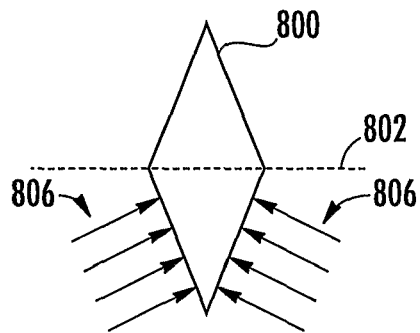
FIG. 8A is a side view of a rotating disk anode according to an embodiment of the subject matter described herein.
Figure 8B:
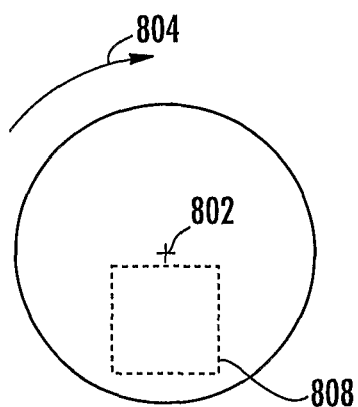
FIG. 8B is a front view of the rotating disk anode shown in FIG. 8A according to an embodiment of the subject matter described herein.

FIGS. 8A and 8B illustrate a side view and a front view, respectively, of a rotating disk anode 800 according to an embodiment of the subject matter described herein. Anode 800 may be disk shaped and rotatable about an axis 802 in the direction indicated by arrow 804 in FIG. 8B. Referring to FIG. 8A, electron beams, generally designated 806, may be applied to two sides of anode 800. Referring to FIG. 8B, an area 808 designates a location bombarded by electrons of electron beams. As disk anode 800 is rotated about axis 802, a different surface portion of anode 800 passes area 808 such that a portion of anode 800 is not continuously bombarded by electrons. As a result, the heat generated by electron bombardment is distributed on the surface of anode 800.

Radiation (RT) Treatment Planning Software (TPS)

RT TPS may be utilized for determining radiation dose amount, dose size, dose shape, and intensity distribution of the radiation field for both pre-clinical and clinical applications. A TPS-based system may simulate an x-ray pixel array system and a patient using 3-D images from CT and other image modalities. Further, a TPS-based system may create a virtual reality environment for use by a planner to design and optimize treatment before actual delivery. An exemplary TPS system is the PLanUNC (PLUNC) software, a National Institutes of Health (NIH) public research tool developed by the University of North Carolina at Chapel Hill.

As stated above, the x-ray pixel array systems and methods described herein may be applied to small-animal models in a pre-clinical setting. Accurate dosimetry is a prerequisite for high precision small-animal irradiation. RT dosimetry calculations for small-animals may include simulation of the x-ray pixel beam array radiation that is produced by a system described herein and calculation of the resulting does in a small animal based on micro-CT images. The micro-CT dose code may be evaluated by phantom tests and compared with the measurement.

Development of Monte Carlo-Based Dosimetry Calculations

Simulation of x-ray pixel beam array radiation can include Monte Carlo calculations for producing highly accurate beam models for accurate dosimetry for both pre-clinical and clinical applications. Beam modeling can require accurate information of the energy and angular distribution of each electron pixel beam, the geometry and materials of the anode, and other relevant information. Simulation of a system described herein can consist of characterization of an electron emitter, characterization of an anode, and characterization of collimator apertures. The spatial, angular, and energy distribution of an electron beam just before hitting the anode may be modeled. Further, the angle and position of the anode may be modeled. Several apertures of a collimator may be modeled for providing full simulation of crosstalk between pixels.

Rather than generating a mathematical description of an x-ray pixel beam, the Monte Carlo simulation can generate a phase space file at a specific location in the x-ray beam path that contains all of the information needed for accurate dose computation downstream. The file can contain information for a large number of individual particles (e.g., x-ray and electron), including the energy, position, and velocity vector of each particle. The file can represent the kV radiation generated by each x-ray pixel beam. The phase space file may be used as input for the dosimetry calculation in the small animal under irradiation.

Micro-RT Small Animal Dosimetry Calculation

Micro-RT dosimetry in the small animal can be calculated using suitable software such as the DOSXYZnrc software, developed by the National Research Council of Canada (NRC) of Ottawa, Canada. DOSXYZnrc is an EGSnrc-based Monte Carlo simulation code for calculating dose distributions in a rectilinear voxel phantom. DOSXYZnrc is part of the OMEGA-BEAM system of codes developed at NRC. Density and material in every voxel may vary. A variety of beams may be incident on the phantom, including full phase-space files from BEAMnrc and beams characterized using beam characterization models. The Hounsfield number of each voxel can be used to determine its material composition. Voxels can be specified as tissue, lung, or bone with the elemental composition of each defined according to International Commission on Radiation Units and Measurements (ICRU) standards and the density of each voxel determined by the specific Hounsfield value. The mouse models may have voxel dimensions as small as 250 microns in the Monte Carlo simulation. DOSXYZnrc software uses the phase space file output from BEAMnrc as its input for dose computation. Because the contents of the phase file is directly related to the incident electron beam current, the absolute dose in each voxel can be fully independent. The cumulative dosimetry is the sum of doses from all active x-ray pixel beams.

Validation of Monte Carlo Dosimetry Calculations

The Monte Carlo model may be validated using gel dosimetry and GAFCHROMIC™ radiochromic dosimetry films. Gel dosimeters react to the passage of ionizing radiation by radiation-induced polymerization that changes the opacity of the gel in proportion to the amount of dose deposited. The resulting changes in opacity can be quantified using optical scanning (e.g., CT or MRI techniques) for producing a 3-D representation of deposited dose which can be evaluated at length scales less than 1 mm. This technique can allow a full 3-D evaluation and validation of the Monte Carlo dosimetry of the x-ray pixel beam array irradiation by the x-ray pixel array system. When exposed to radiation, acid in the emulsion undergoes a solid-state polymerization producing a blue dye polymer that changes the optical absorption property of the film. The GAFCHROMIC™ films provide inherently high spatial resolution and are not sensitive to light. An optical scanner of high resolution can read out absolute radiation dose and relative dose distributions. Single x-ray pixel dose distribution and dose distributions from selected x-ray pixel beam array patterns may be validated.

RT treatment optimization can be applied to the systems and methods described. RT treatment optimization is an automated treatment planning technique that prescribes the treatment delivery parameters that are specific to the subject under irradiation and optimized to the given treatment goal. This dose optimization algorithm may be used for fully utilizing the potential of electronic definition of radiation field shape and intensity distribution inherent in the systems described herein.

Optimization may be implemented by application of an index-dose gradient minimization algorithm and/or other optimization algorithms to the micro-RT treatment planning, implementation of new optimization objectives, and evaluation. In the index-dose gradient minimization algorithm, the x-ray beam intensity may be adjusted based on the dose calculation points the beam traverses and the adjustment is based on the collective need of all dose points to reach optimization. The x-ray pixel beam intensity can be determined collectively by all of the point doses along its path.

Dose volumetric optimization may be provided by a TPS system. A planner may define one or more anatomical structures of interest, such as a tumor and structures to spare, on a 3-D image set and specify the goal dose volume histogram for each anatomical structure of interest. Further, a goral dose volume histogram may be specified for each anatomical structure of interest. Other applications of index distributions can define different optimization objectives. For example, a biomarker can be used for imaging particular tumor cells in a small animal and the image can represent the tumor cell density.

Figure 9A:
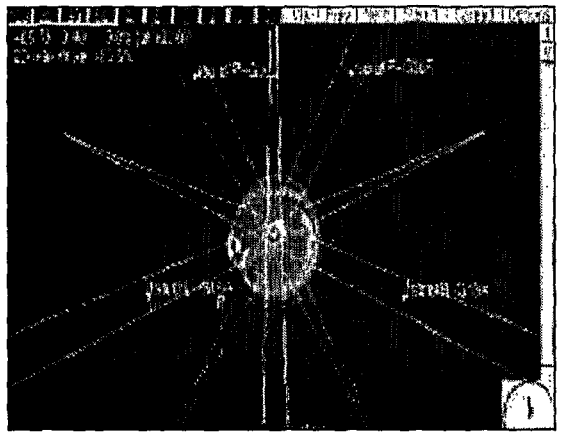
FIGS. 9A and 9B are screen displays showing a treatment planning software (TPS) system simulation of micro-RT treatment planning on a mouse CT image according to the subject matter described herein.
Figure 9B:
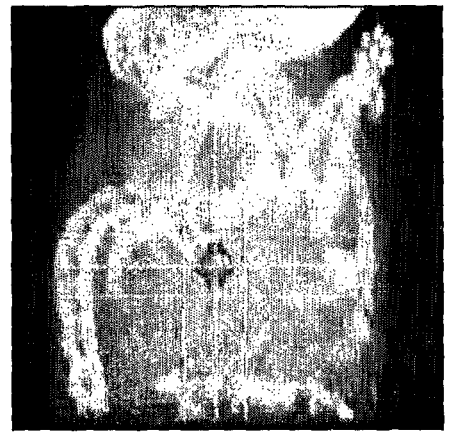

FIGS. 9A and 9B are screen displays showing a TPS system simulation of micro-RT treatment planning on a mouse CT image according to the subject matter described herein. A simulated tumor is delineated in the lung region of the mouse and a radiation field is designed to cover the tumor with a predetermined margin. FIG. 9A shows a simulated micro-RT treatment beam set-up on the micro-CT image of the mouse using the TPS system. FIG. 9B shows a micro-RT radiation field portal superimposed on a micro-CT image of the mouse.

Figure 10:
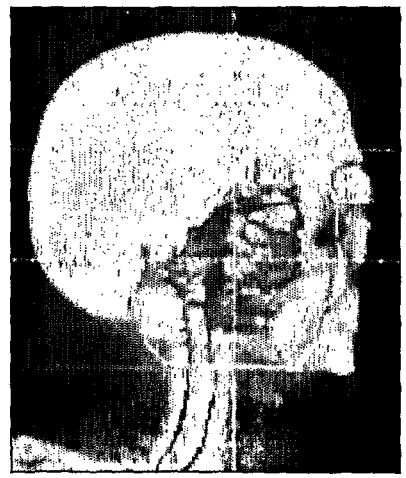
FIG. 10 is an image of a beam's eye-view (BEV) of nasopharynx cancer treatment according to the subject matter described herein.

FIG. 10 illustrates an image showing dose optimization in a clinical setting according to the subject matter described herein. FIG. 10 is an image of a BEV of nasopharynx cancer treatment.

FIG. 11A illustrates a graph of a goal DVH curve and the current DVH that changes in the optimization. The DVH curve is the inverse of the index-dose curve. The iterative optimization process moves the dose grid points whose current dose values are A toward B. The current DVH curve horizontally approaches the goal DVH curve until the optimization converges.

FIG. 11B illustrates intensity maps of a radiation field after n iterations in the optimization, wherein n=0, 2, 5, 10 and 15.

X-Ray Pixel Beam Array Systems and Methods for Clinical Applications

As stated above, the subject matter described herein includes x-ray pixel beam array systems for clinical applications. Clinical applications may be characterized by the generation of x-rays having energy on the order of mega electron volts (MeV).

Figure 12:
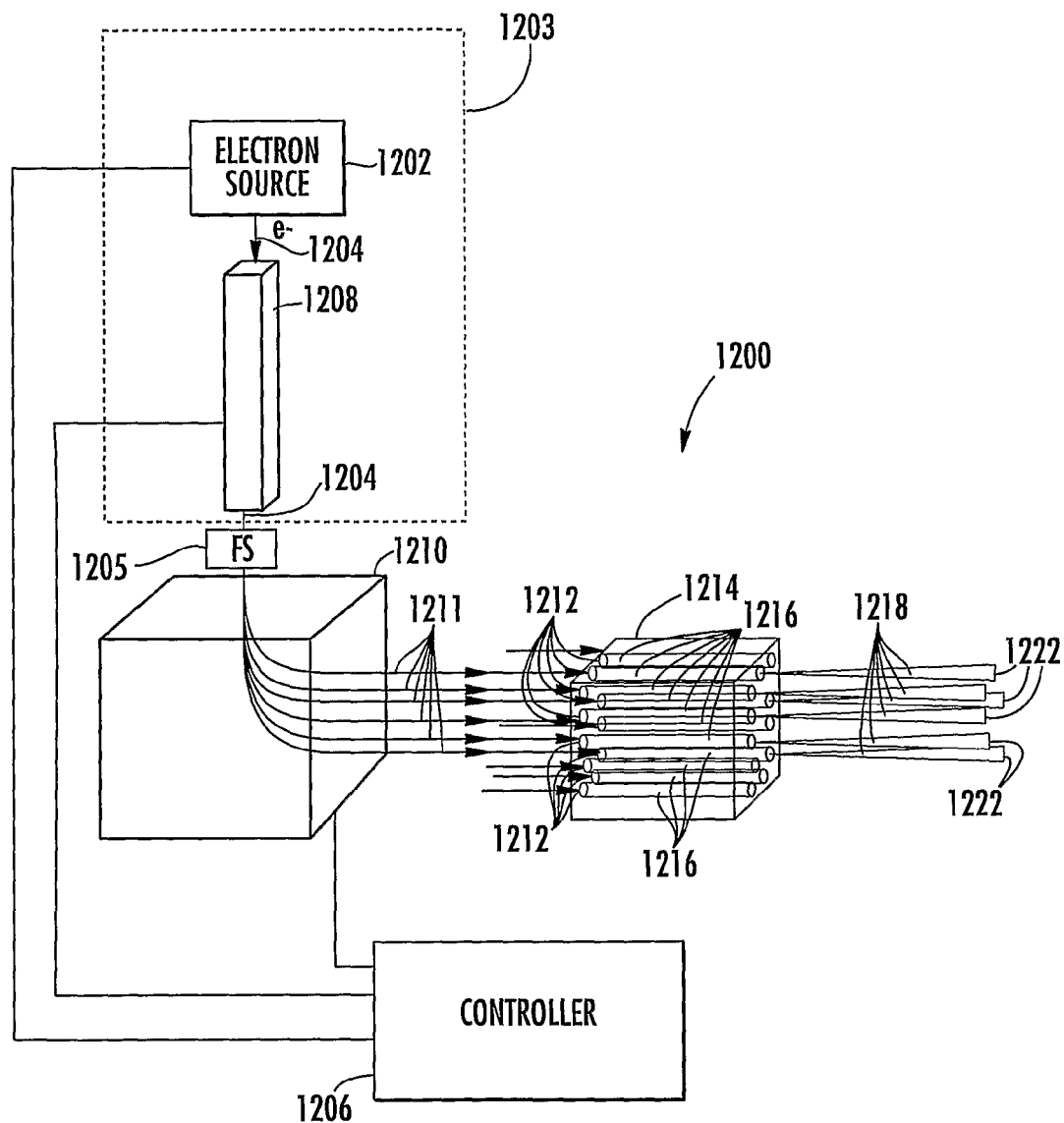
FIG. 12 is a schematic, perspective side view of an x-ray pixel array system according to an embodiment of the subject matter described herein.

FIG. 12 illustrates a schematic, perspective side view of an x-ray pixel array system for clinical applications generally designated 1200 according to an embodiment of the subject matter described herein. Referring to FIG. 12, system 1200 may include an electron source 1202 operable to emit an electron beam 1204. A controller 1206 may control electron source 1202 to pulse electron beam 1204. Electron beam 1204 may be pulsed at a rate corresponding to the capabilities of electron source 1202. Electron beam 1204 may be on the order of kV.

A linear accelerator 1208 may receive electron beam 1204 and accelerate at least a portion of the electrons associated with electron beam 1204. The energy of an electron beam from linear accelerator 1208 may be two MeV to about 100 MeV. The electron beam produced by accelerator 1208 may be pulsed at tens of hertz to hundreds of hertz. The pulse rate and the pulse pattern may be controlled by controller 1206.

In one example, electron source 1202 and linear accelerator 1208 may be a pulsed MeV electron beam source 1203. Source 1203 may include a low energy electron source and a related MeV linear accelerator. For example, such a combined device is available from Siemens AG of Berlin, Germany), Varian, Inc. of Palo Alto, Calif., Elekta AB of Stockholm, Sweden, and TomoTherapy Incorporated of Madison, Wis. Source may be operable to produce a pulsed electron beam.

Electron beam 1204 output from linear accelerator 1208 may be received by a focusing system 1205. Focusing system 1205 may consist of a plurality of quadrupole magnets that provide focusing of electron beam 1204 at a location of x-ray targets described below.

A scanning system 1210 may receive electron beam 1204 for scanning electron beam 1204 for sending electron beam 1204 along a plurality of paths 1211 for receipt by x-ray targets 1212. Targets 1212 may be a transmission x-ray target for generating x-ray beams by Bremsstrahlung production such that the x-ray beams travel in the same direction as the electrons after bombarding the anode. Controller 1206 may control scanning system 1210 to scan electron beam 1204 along the different paths 1211. According to the subject matter described herein, scanning system 1210 and controller 1206 preferably control the scanning of electron beams electronically with no moving components. In one embodiment, as will be described in more detail below, scanning system 1210 may include a two-stage magnetic scanning system having magnets controlled by controller 1206 to selectively scan each electron beam along a predetermined path.

X-ray targets 1212 may be positioned to receive a scanned electron beam and to convert at least a portion of energy associated with the electron beam to an x-ray beam. X-ray targets 1212 may be made of any suitable material for converting an electron beam to an x-ray beam. Exemplary x-ray target materials include tungsten, gold and molybdenum. X-ray targets 1212 may be attached to an x-ray pixel collimator 1214 or positioned near collimator 1214.

Collimator 1214 may include a plurality of apertures 1216 extending between ends of collimator 1214 for collimating x-ray beams from x-ray targets 1212. Each aperture 1216 may be associated with a respective target 1212 for receiving an x-ray beam from the target. Each aperture 1216 may be substantially straight. Further, each aperture 1216 may be tapered or conical in shape. Collimator 1214 may produce a plurality of collimated x-ray beams 1218 for irradiating predetermined locations 1222. X-ray beams produced by collimator 1214 may have a maximum energy between about a 2 and 100 MeV depending on linear accelerator 1208.

Scanning system 1210 may bend and align electron beam 1204 with any of apertures 1216 to produce a specific x-ray pixel beam pattern according to a treatment/patient specific plan created by radiotherapy treatment planning and optimization software. The operation of scanning system 1210 and electron source 1208 may be controlled by controller 1206. Controller 1206 may execute software instructions for performing a sequence by which locations and/or subjects are irradiated by collimated x-ray beams output by collimator 1214. For example, controller 1206 may control scanning system 1210 to direct pulsed electron beam 1204 to different apertures 1216 of collimator 1214 such that different predetermined locations 1222 are selectively irradiated by an output collimated x-ray beam in a time sequence. Controller 1206 may control scanning system to direct electron beam 1204 along paths 1211 in sequence for receipt by apertures 1216 such that respective predetermined locations 1222 are irradiated in sequence. The executable instructions may be performed for controlling scanning of electron beam 1204 such that corresponding collimated x-rays are applied to predetermined locations for predetermined durations and radiation dosages in a predetermined sequence.

The executable instructions of controller 1206 may be implemented using industrial input and output (I/O) analog and digital boards, pulse generators, timing modules, embedded computer systems, and user interface computers.

Figure 13:
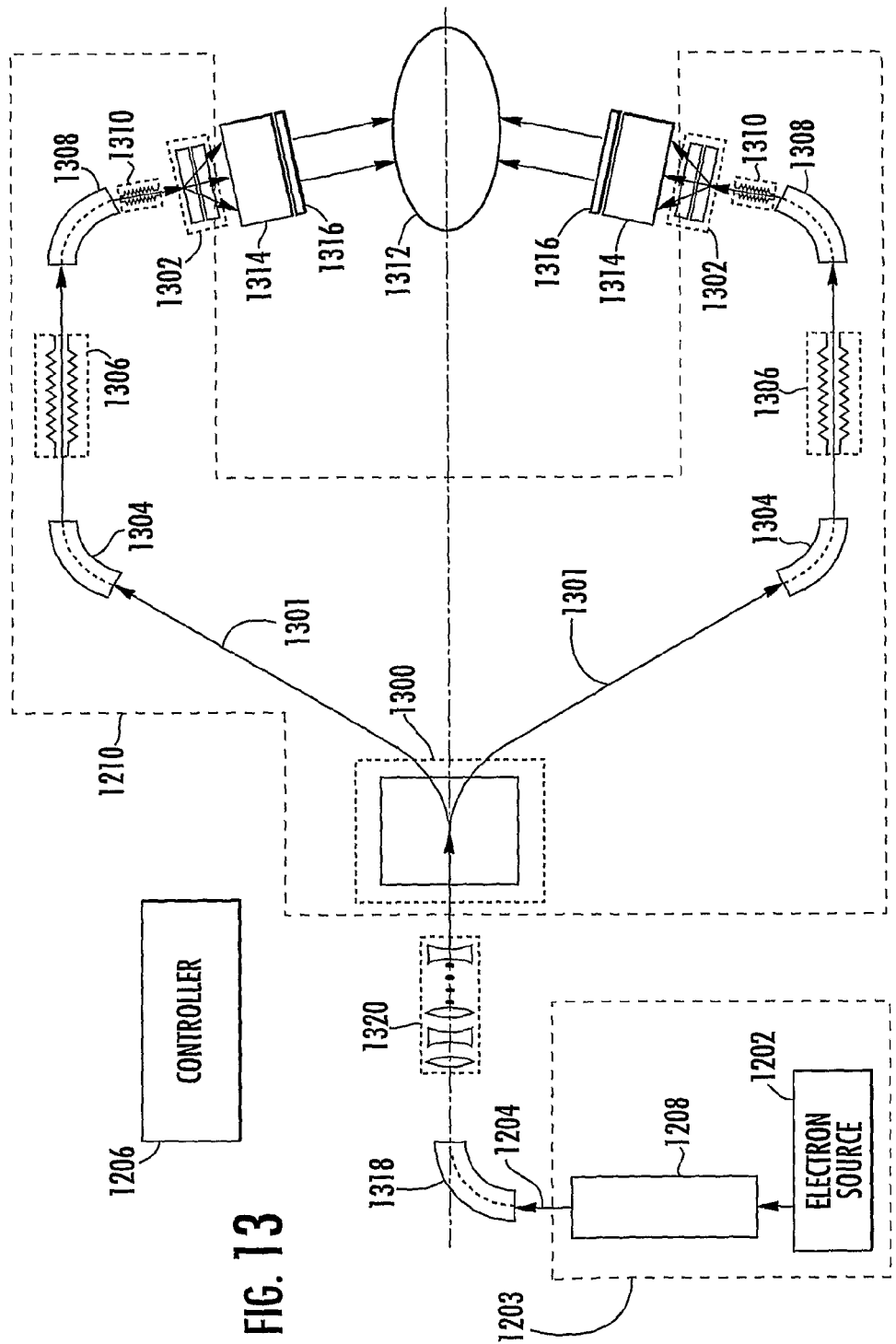
FIG. 13 is a schematic side view of an x-ray pixel array system according to an embodiment of the subject matter described herein.

FIG. 13 illustrates a schematic side view of an x-ray pixel array system 1200, illustrating more details of scanning system 1210 according to an embodiment of the subject matter described herein. In FIG. 13, system 1200 includes components 1202, 1206, 1208, and 1210 described with regard to FIG. 12. In FIG. 13, scanning system 1210 includes first and second stages and 1300 and 1302 as well as additional components 1300, 1302, 1304, 1306, 1308, 1310, 1314, 1318, and 1320 for scanning electron beams along predetermined paths for generating x-ray beams. In the illustrated example, first stage scanning system 1300 may include one or more magnets that direct electron beams to a plurality of electron beam channels 1301 connected to system 1200. Electron beam channels 1301 are fanned out in a conical configuration to send electron beam 1204 to multiple directions to provide a complete 360° angular coverage for a subject 1312 being treated. For each electron beam channel 1304, two bending magnets 1304 and 1308 are used to bring the electron beam from first stage scanning system 1300 towards second stage scanning systems 1302.

Vacuum bellows 1306 provide horizontal length adjustment for positioning the x-ray beams with respect to subject 1312. Vacuum bellows 1310 provide angular adjustments for the electron beam and thus the center direction of the x-ray beam generated by collimators 1314. Both mechanical adjustments enabled by vacuum bellows 1306 and 1310 may be one-time adjustments performed before the start of the treatment when necessary. Vacuum bellows 1306 and 1310 may remain at fixed positions during treatment.

Second-stage scanning systems 1302 receive the electron beams from vacuum bellows 1308 and scan the electron beams in two dimensions across the surfaces of collimators 1314. Collimators 1314 may include a plurality of holes or apertures for electron beams. Exemplary configurations for collimators 1314 will be described in detail below. In therapeutic applications, x-ray targets may be included at the ingress point of each collimator aperture to generate x-rays corresponding to the electron beams. In imaging applications, electron targets may be included at the egress point of each collimator aperture. Dose measurement systems 1316 may be provided at the egress locations of each collimator 1314 to measure the radiation dose being delivered to subject 1312.

In operation, electron source 1202 and accelerator 1208 may generate MeV electron beams at a predetermined frequency. A bending magnet 1318 may direct the electron beams in the direction of first stage scanning system 1300. Focusing system 1320 may focus the electron beams in the direction of collimators 1314. First stage scanning system 1300 may direct one or more electron beam pulses to one of bending magnets 1304. The electron beams then proceed through components 1306, 1308, and 1310 to second stage scanning system 1302. Second stage scanning system 1302 may be controlled by controller 1206 to direct each electron beam pulse to a desired location in collimator 1314. A target at the ingress point of the desired collimator aperture may convert the electron to an x-ray pulse. The x-ray may proceed through the aperture of collimator 1314. The x-ray may impact subject 1312 in a desired location.

Figure 14:
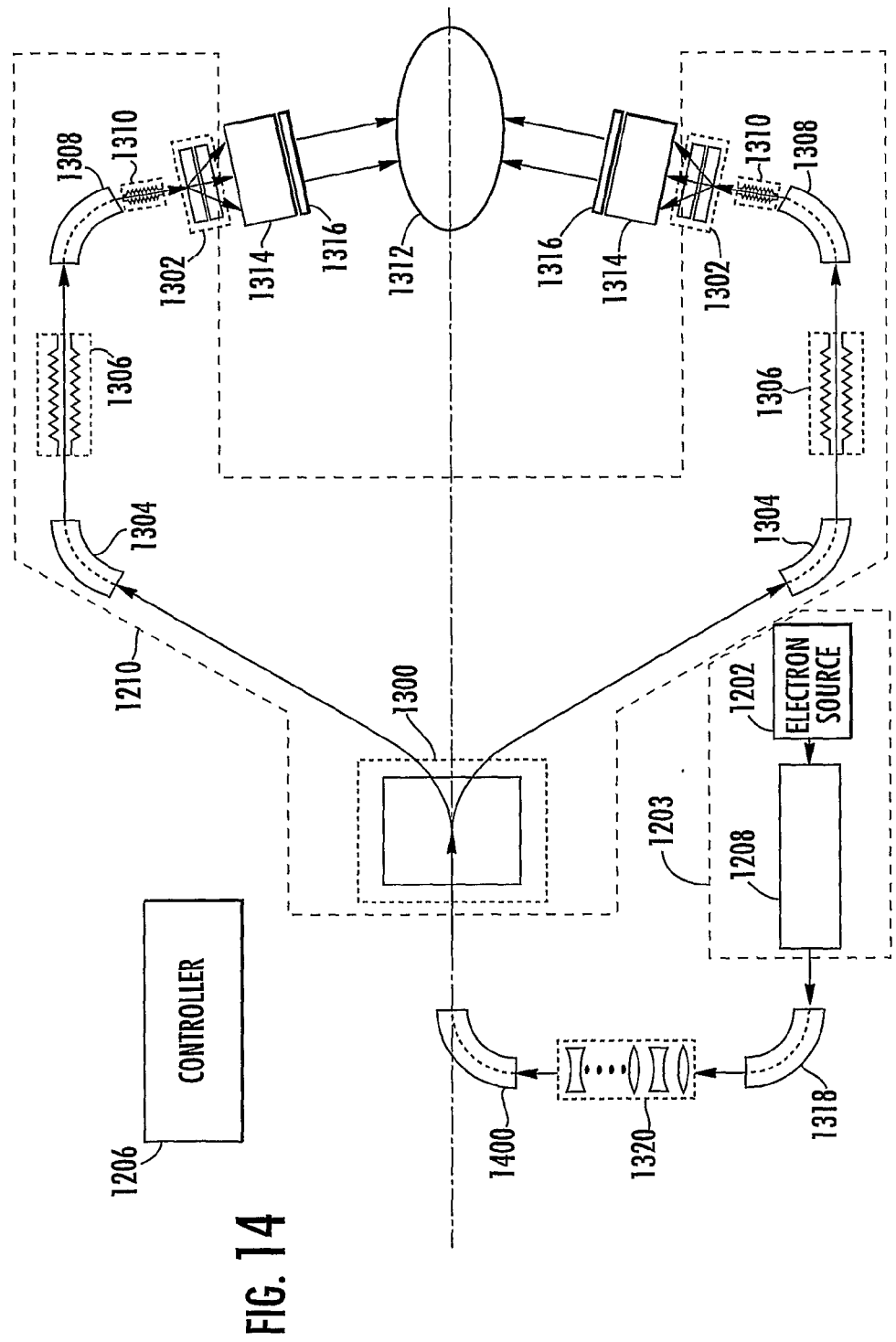
FIG. 14 is a schematic side view of an x-ray pixel array system according to another embodiment of the subject matter described herein.

In the example illustrated in FIG. 13, source 1202 and linear accelerator 1208 are arranged vertically with respect to first-stage scanning system 1300. In an alternate implementation, shown in FIG. 14, electron source 1202 and/or linear accelerator 1208 may be arranged horizontally and may be located below system 1300 to save horizontal space in a room in which system 1200 is deployed. In FIG. 14, an additional bending magnet 1400 is included to bend the electron beams in the direction of scanning system 1400. Other than the positioning of source 1202 and accelerator 1208 and the addition of bending magnet 1400, the operation of the system illustrated in FIG. 14 is the same as that illustrated in FIG. 13. Hence, a description thereof will not be repeated herein.

Figure 15:
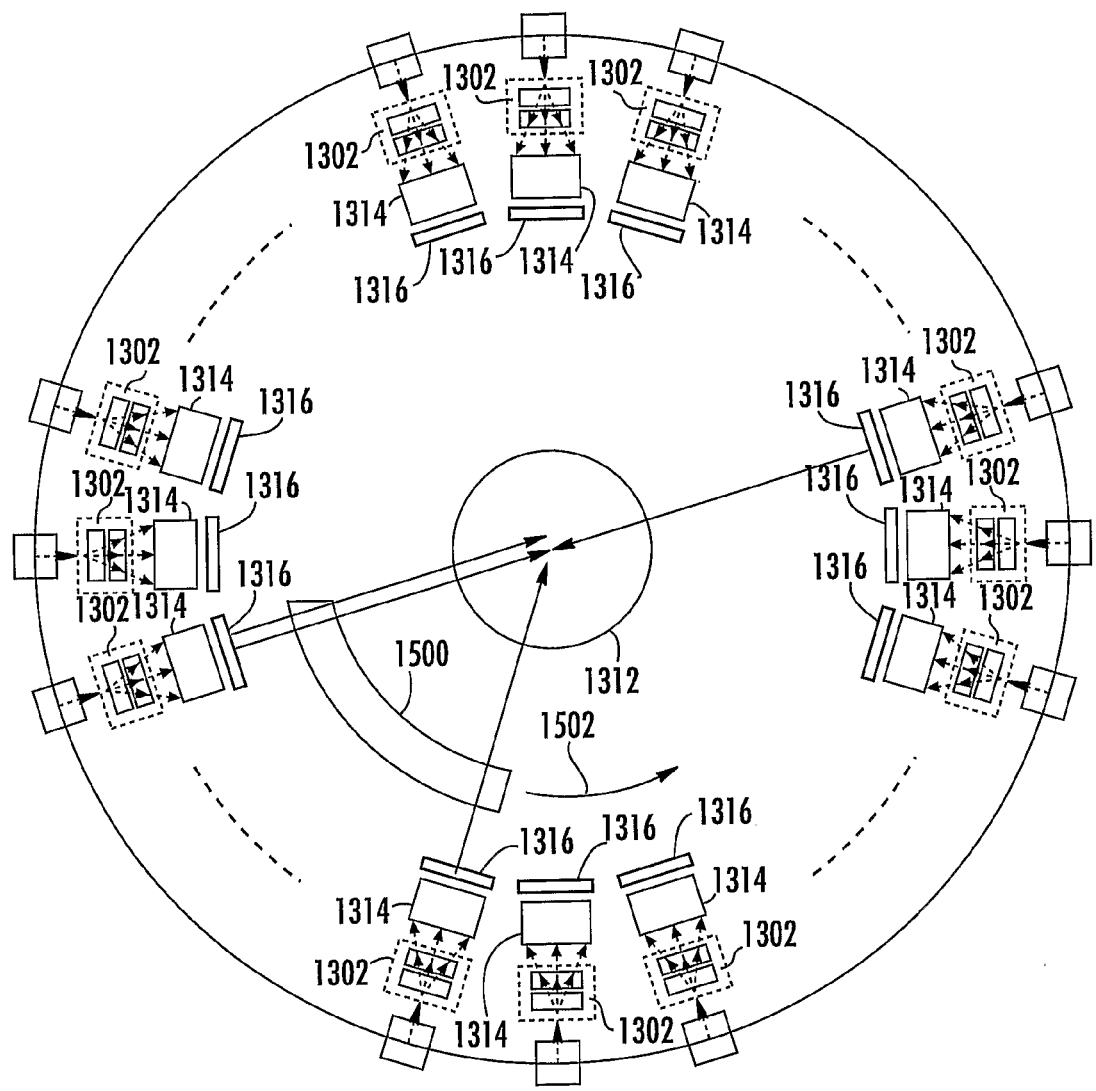
FIG. 15 is a schematic, cross-sectional front view of a configuration of second-stage scanning magnets, x-ray pixel array collimators, and radiation measurement systems of the x-ray pixel array system shown in FIG. 13 with respect to a subject being treated or imaged according to an embodiment of the subject matter described herein.

FIG. 15 illustrates a schematic, cross-sectional front view of a configuration of second-stage scanning systems 1302, x-ray pixel array collimators 1314, and radiation measurement systems 1316 of x-ray pixel array system 1200 with respect to subject 1312 according to an embodiment of the subject matter described herein. Referring to FIG. 15, scanning magnets 1302, collimators 1314, and radiation measurement systems 1316 may be configured in a concentric pattern for surrounding subject 1312 in a 360° manner. Collimators 1314 may be oriented such that output x-ray beams impact subject 1312 at a desired angle. In one exemplary implementation, collimators 1314 may be tilted to vary the angle and location at which x-rays impact subject 1312 using adjustable vacuum bellow 1310. Aperture patterns for collimator 1314 may vary depending on the desired radiation dose granularity and pattern. Exemplary collimator aperture patterns suitable for use with embodiments of the subject matter described herein will be described in detail below.

X-ray pixel array system 1200 may include a CT x-ray imaging plate 1500. Plate 1500 may be rotatable in a direction indicated by arrow 1502 about the center of the concentric pattern formed by scanning magnets 1302, collimators 1314, and radiation measurement systems 1316. Plate 1500 may be operable to detect x-ray beams generated by system 1200 for use in producing a three-dimensional (3-D) image of subject 1312.

Controller 1206 may execute instructions for performing a sequence of x-ray pixel beam irradiation to subject 1312 by system 1200. The sequence may be defined by a selected set of x-ray pixel beams at different portals and the selected duration of each x-ray pixel beam. Controller 1206 may control source 1202 to generate different patterns of the electron beam pulses. Scanning magnets 1300 and 1302 of the two-stage scanning system may direct the pulses to particular apertures of collimators 1314 to produce x-ray beams for irradiating the predetermined locations.

The electron beam paths in system 1200 are vacuum sealed. For example, the electron beam path between source 1202 and x-ray target 1302 is vacuum sealed.

Figure 16:
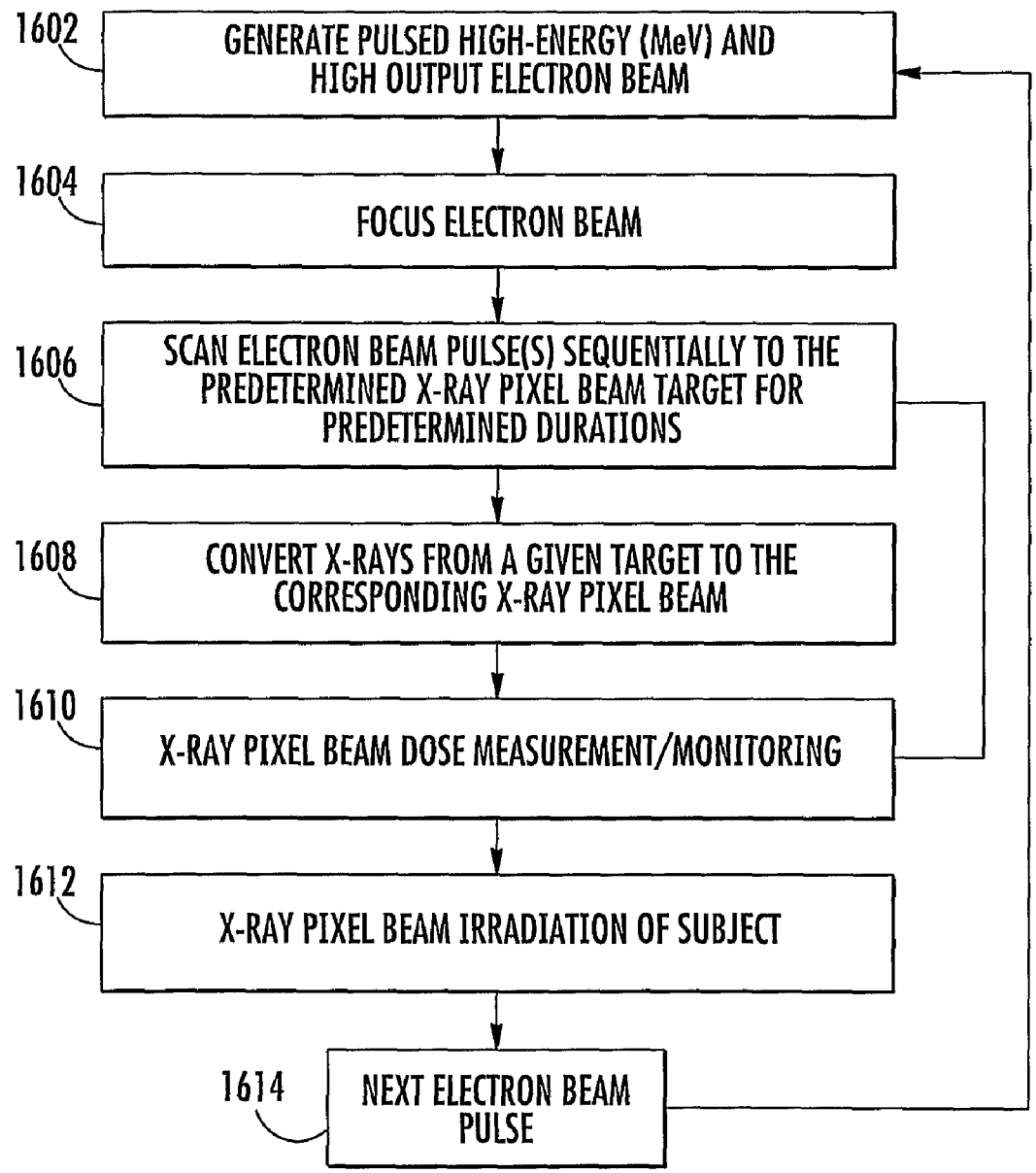
FIG. 16 is a flow chart illustrating an exemplary process for irradiating predetermined locations on a subject with the x-ray pixel array system shown in FIGS. 13-15 according to an embodiment of the subject matter described herein.

FIG. 16 is a flow chart illustrating an exemplary process for irradiating predetermined locations on subject 1312 with x-ray pixel array system 1200 shown in FIGS. 13-15 according to an embodiment of the subject matter described herein. Referring to FIG. 16, source 1203 may generate a pulsed high-energy (MeV) and high output electron beam (block 1602). The pulsed electron beam may be accelerated by a linear accelerator to two and one hundred MeV. In block 1604, the electron beam may be focused by focusing system 1320.

In block 1606, the electron beam may be scanned by the two-stage scanning system to one of the x-ray pixel beam targets for conversion to an x-ray beam. Alternatively, a scanning system with more than two stages may be used, depending on the complexity of the electron beam path and the need for covering a large treatment area. First-stage scanning system 1300 may scan each electron pulse to second-stage scanning systems 1302. Systems 1302 may surround subject 1312. Each system 1302 may scan the electron beam to a desired x-ray pixel beam target at the entrance of collimators 1314 to produce a desired x-ray pixel beam.

In block 1608, the intrinsic x-ray beam is collimated to convert x-rays from a target to a corresponding x-ray pixel beam. For example, the x-ray beam may be passed through one of the apertures in the x-ray pixel array collimator 1314.

In block 1610, the radiation dose and location generated by the x-ray pixel beam is measured and the result is transferred to the control system 1606 for radiation control. In block 1612, the x-ray beam is delivered to a predetermined location of subject 1312. For example, each electron pulse may be scanned such that an x-ray pixel beam from an aperture of collimator 1314 is delivered to a desired treatment or imaging location of subject 1312.

In block 1614, the next pulse is generated, and blocks 1602 through 1612 are repeated to scan the next pulse to generate an x-ray beam at a desired location of subject 1312.

FIG. 16 shows a particular scheme of scanning one individual electron beam pulse and delivering the resultant plurality of pulsed x-ray pixel beams to the subject. In FIG. 16 this procedure can be repeated for each individual pulse of electron beam. This scheme may also be modified to scan and deliver a number of pulses, the number of pulses is more than one, to the same predetermined treatment area as determined by the treatment dose plan and as controlled by controller 1206.

Figure 17:
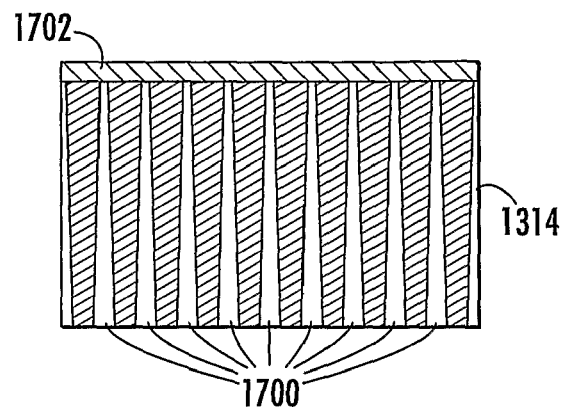
FIG. 17 is a cross-sectional side view of a collimator according to an embodiment of the subject matter described herein.

FIG. 17 illustrates a cross-sectional side view of collimator 1314 according to an embodiment of the subject matter described herein. Referring to FIG. 17, collimator 1314 includes a plurality of apertures 1700 extending through collimator 1314. Apertures 1700 may be tapered or conical in shape. For therapeutic applications, a target 1702 may be positioned at input ends of apertures 1700 for x-ray pixel beam collimation. Target 1702 may be tungsten or other material that is capable of converting electron beams into x-rays. Target 1702 may substantially cover the surface of collimator 1302. Alternatively, individual targets may cover each aperture 1700. For imaging applications, target 1702 may be included at the egress points of apertures 1700 to produce wider-angle x-ray beams for imaging purposes.

Figure 18A:
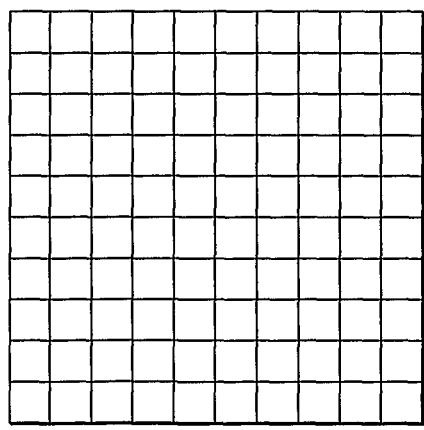
FIG. 18A is a top view of an exemplary collimator according to an embodiment of the subject matter described herein.

As stated above, collimator apertures may be configured in any suitable pattern, depending on the desired resolution and shape of the radiation pattern desired and the treatment delivery time requirement. For example, collimator apertures may be configured with high-density, small apertures to produce high spatial resolution radiation field shapes and intensity patterns. In another example, collimator apertures of a range of sizes and shapes can be used to accommodate a combination of considerations of both dose delivery resolution and time. FIG. 18A illustrates a top view of an exemplary collimator 1314 where each square represents the area for a collimator aperture. In the example illustrated in FIG. 18A, collimator apertures are of equal cross-sectional area, to deliver a substantially uniform radiation dose to the corresponding areas of a subject 1312.

Figure 18B:
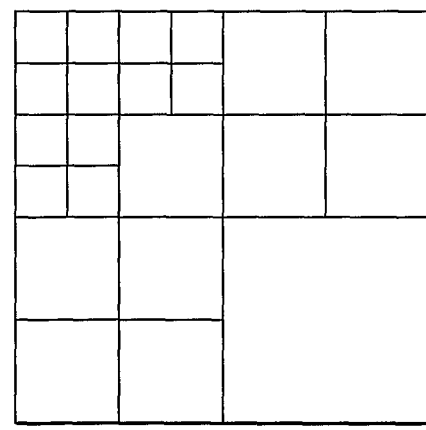
FIG. 18B is a top view of another exemplary collimator according to an embodiment of the subject matter described herein.

FIG. 18B is a top view of collimator 1314 illustrating another exemplary pattern. In FIG. 18B, the cross-sectional areas of the various apertures are different. Such a pattern would deliver radiation to a subject at different levels of granularity. For example, x-ray pixels could be delivered at locations of a subject corresponding to the smaller apertures with high resolution or resolution. X-ray pixels could be delivered at areas of a subject with lower resolution in the areas of collimator 1314 with larger-diameter apertures. As stated above, collimators may be interchangeable to generate different patterns for different therapeutic and imaging applications. Furthermore, collimator 1314 with varying aperture sizes as shown in FIG. 18B may be mounted with different orientations to provide better coverage of the treatment area.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A clinical x-ray pixel array system comprising:
   (a) a pulsed MeV electron beam source including a linear accelerator operable to produce a pulsed electron beam;
   (b) an n-stage scanning system operable to scan the electron beam along a path, n being an integer of at least two;
   (c) a plurality of x-ray targets positioned to convert the electron beam to x-rays;
   (d) an x-ray pixel array collimator positioned downstream of the x-ray targets to collimate the x-rays from one of the x-ray targets for producing an x-ray pixel beam, wherein the collimator comprises a plurality of apertures, and wherein the n-stage scanning system is operable to selectively scan and aim the electron beam at predetermined apertures of the collimator; and
   (e) a controller operable to control the pulsation of the electron beam source and the n-stage scanning system for sequentially generating a predetermined spatial and temporal x-ray pixel beam array pattern.

2. The system of claim 1 wherein the linear accelerator is operable to pulse the electron beam at a frequency of tens of hertz to hundreds of hertz.

3. The system of claim 1 wherein the linear accelerator is operable to accelerate the electron to an energy of between two MeV and about 100 MeV.

4. The system of claim 1 wherein the n-stage scanning system includes a plurality of magnets for directing the electron beam to a desired location.

5. The system of claim 1 wherein the n-stage scanning system includes a first-stage scanning system and a plurality of second-stage scanning systems, wherein the first-stage scanning system is operable to selectively scan the electron beam for receipt by one of the second-stage scanning systems.

6. The system of claim 5 comprising magnetic devices for directing the electron beam to predetermined locations.

7. The system of claim 5 wherein the x-ray pixel array collimator comprises a plurality of x-ray pixel array collimators positioned downstream of the second stage scanning systems, wherein each of the second-stage scanning systems is operable to selectively scan and aim the electron beam at predetermined apertures of an associated collimator.

8. The system of claim 7 comprising a plurality of x-ray targets positioned at an ingress side of the collimators and the second stage scanning systems for converting at least a portion of energy associated with the electron beam hitting the target to an x-ray beam.

9. The system of claim 1 wherein the controller is operable to control the timing, pulse rate, and duration of the electron beam produced by the electron beam source.

10. The system of claim 1 wherein the controller is operable to control an absolute dose, size, shape, and/or intensity distribution of a radiation field produced by x-ray beam produced by the collimator.

11. The system of claim 1 wherein the controller is operable to control the n-stage scanning system to scan the pulsed electron beam such that pulses of the pulsed electron beam are selectively input into predetermined apertures of the plurality of apertures.

12. The system of claim 1 wherein the apertures form a pattern corresponding to a desired x-ray irradiation resolution and efficiency.

13. The system of claim 12 wherein the collimator is interchangeable with other collimators of different patterns for providing different radiation resolution and efficiency.

14. The system of claim 1 wherein the n-stage scanning system includes a vacuum bellow system for adjusting the positions of the x-ray pixel beam with respect to a subject.

15. A pixel array system for imaging a subject, the system comprising:
   (a) a pulsed MeV electron beam source including a linear accelerator operable to produce a pulsed electron beam;
   (b) an n-stage scanning system operable to scan the electron beam along a path, n being an integer of at least two;
   (c) a plurality of x-ray targets positioned to receive the electron beam and convert at least a portion of energy associated with the electron beam to imaging x-ray beams from different predetermined directions;
   (d) a controller operable to control the pulsation of the electron beam source and operable to control the scanning system for producing imaging x-ray beams from the predetermined directions to image a subject;
   (e) an x-ray pixel array collimator comprising a plurality of apertures, wherein the n-stage scanning system is operable to selectively scan the electron beam for receipt by one of the apertures of the collimator; and
   (f) a rotating x-ray image plate for image acquisition of the subject.

16. The system of claim 15 wherein the n-stage scanning system includes a first-stage scanning system and a plurality of second-stage scanning systems, wherein the first scanning system is operable to selectively scan the electron beam for receipt by the second-stage scanning systems.

17. The system of claim 16, wherein the x-ray pixel array collimator comprises a plurality of x-ray pixel array collimators each including a plurality of apertures, and wherein each of the second-stage scanning systems is operable to selectively scan the electron beam for receipt by one of the apertures of an associated collimator.

18. The system of claim 15 wherein the controller is operable to control the timing and pulse rate and duration of the electron beam produced by the electron beam source.

19. The system of claim 15 wherein the controller is operable to control the scanning system for delivering the imaging x-ray beams to predetermined directions where the imaging detector is located.

20. The system of 15 wherein the imaging detector is controlled by the controller to mechanically rotate to a position to receive the imaging x-ray beams for imaging.

21. A method for selectively irradiating predetermined x-ray pixel beams, the method comprising:
   (a) emitting and accelerating a pulsed electron beam;
   (b) scanning the electron beam along a path using an n-stage scanning system, n being an integer of at least two;
   (c) converting at least a portion of energy associated with the electron beam to an x-ray beam;
   (d) collimating the x-ray beam to produce a collimated x-ray pixel beam, wherein collimating the x-ray beam comprises providing an x-ray pixel array collimator comprising a plurality of apertures, and wherein scanning the electron beam along a path comprises operating the n-stage scanning system to selectively scan the electron beam for receipt by one of the apertures of the collimator; and
   (e) controlling the scanning system for selectively irradiating the predetermined x-ray pixel beams with the collimated x-ray pixel beam.

22. The method of claim 21 wherein emitting a pulsed electron beam includes emitting a pulsed electron beam at a frequency of tens hertz to hundreds hertz.

23. The method of claim 21 wherein accelerating a pulsed electron beam includes accelerating a pulsed electron beam to an energy of between two MeV and about 100 MeV.

24. The method of claim 21 wherein scanning the electron beam includes providing a two-stage scanning system comprising a first-stage scanning system and a plurality of second-stage scanning systems, wherein the first-stage scanning system is operable to selectively scan the electron beam for receipt by one of the second-stage scanning systems.

25. The method of claim 24 wherein providing an x-ray pixel array collimator comprises providing a plurality of x-ray pixel array collimators each including a plurality of apertures, and wherein each of the second-stage scanning systems is operable to selectively scan the electron beam for receipt by one of the apertures of an associated collimator.

26. The method of claim 25 converting at least a portion of energy includes providing a plurality of x-ray targets positioned between the collimators and the second-stage scanning systems for converting at least a portion of energy associated with the electron beam to an x-ray beam.

27. The method of claim 21, wherein scanning the electron beam includes magnetically directing the electron beam to a desired location.

28. The method of claim 21 comprising controlling the intensity, timing, and pulse rate and duration of the electron beam.

29. The method of claim 21 comprising controlling an absolute dose, size, shape, and/or intensity distribution of a radiation field produced by the electron beam.

30. The method of claim 21 wherein the method comprises providing an n-stage scanning system to scan the pulsed electron beam such that pulses of the pulsed electron beam are sequentially input into predetermined apertures of the plurality of apertures.

31. A method for imaging a subject, the method comprising:
   (a) emitting and accelerating a pulsed electron beam;
   (b) scanning the electron beam along a path using an n-stage scanning system, n being an integer of at least two;
   (c) collimating the x-ray beam and thereby producing a collimated electron beam, wherein collimating the x-ray beam comprises providing an x-ray pixel array collimator comprising a plurality of apertures, and wherein scanning the electron beam along a path comprises operating the n-stage scanning system to selectively scan the electron beam for receipt by one of the apertures of the collimator;
   (d) converting at least a portion of energy associated with the collimated electron beam to an x-ray beam for imaging a subject; and
   (e) detecting the x-ray beam for producing an image of the subject.

32. The method of claim 31 wherein scanning the electron beam includes scanning the electron beam using a first-stage scanning system and a plurality of second-stage scanning systems, wherein the first-stage scanning system is operable to selectively scan the electron beam for receipt by one of the second-stage scanning systems.

33. The method of claim 32 wherein providing an x-ray pixel array collimator comprises providing a plurality of x-ray pixel array collimators each including a plurality of apertures, and wherein each of the second-stage scanning systems is operable to selectively scan the electron beam for receipt by one of the apertures of an associated collimator.

34. The method of claim 31 wherein converting at least a portion of energy includes providing a plurality of x-ray targets for converting at least a portion of energy associated with the electron beam to an x-ray beam.

35. The method of claim 31 wherein scanning the electron beam includes magnetically directing the electron beam to a desired location.

* * * * *